US007041441B1

(12) United States Patent
Steven et al.

(10) Patent No.: US 7,041,441 B1
(45) Date of Patent: May 9, 2006

(54) PHAGE DISPLAY OF INTACT DOMAINS AT HIGH COPY NUMBER

(75) Inventors: Alasdair C. Steven, Silver Spring, MD (US); Paul T. Wingfield, Bethesda, MD (US); Lindsay W. Black, Baltimore, MD (US); Zhaojun Ren, Elkridge, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/837,301

(22) Filed: Apr. 11, 1997

(51) Int. Cl.
  *C12Q 1/00* (2006.01)
  *G01N 33/53* (2006.01)
(52) U.S. Cl. ............................... 435/5; 435/6; 435/7.1; 435/7.21; 435/7.32; 435/69.1; 435/69.7; 435/172.3; 435/173.3; 435/252.3; 435/320.1; 435/456; 436/500; 424/184.1; 514/1
(58) Field of Classification Search ............... 435/5, 435/6, 7.1, 7.32, 7.21, 172.3, 320.1, 456, 435/69.7, 252.3, 691; 514/1; 530/350, 300; 436/500; 424/184.1
See application file for complete search history.

(56) References Cited

U.S. PATENT DOCUMENTS 5,403,484 A * 4/1995 Ladner et al. ............ 435/235.1
5,516,637 A   5/1996 Huang et al. ................. 435/6

OTHER PUBLICATIONS

MacDonald et al., "Regulation of a new bacteriophage T4 gene, 69, that spans an origin of DNA replication.", Embo Journal, Dec. 1, 1984, vol. 3, No. 12, pp. 2863-2671. Abstract Only.*
U. Aebi et al., "Capsid fine stricture of t-eleven bacteriophages.," Journal of Molecular Biology, 1977, vol. 110, pp. 687-698.*
Ren et al., "Phage display of intact domains at high copy number: a system based on SOC, the small outer capsid protein of bacteriophage T4.", Protein Science, 1996, vol. 5., pp. 1833-1843.*
Huang et al., "A small, high-copy-number vector suitable for both in vitro and in vivo gene expression.", Gene, 151, 1994, pp. 143-145.*
Aebi et al., Capsid Fine structure of T-even Bacteriophages, Binding and Localization of Two Dispensable Capsid Proteins . . . , J. Mol. Biol., 110: 687-698 (1977).
Aebi et al., Comparison of the Structural and Chemical Composition of Giant T-even Phage Heads, J. Supramol. Struct., 5:475-495 (1976).
Baldwin et al., Recent Advances in the Generation of Small-Molecule Combinatorial Libraries: Encoded Split Synthesis . . . , Med. Research Rev., 16:391-405 (1996).
di Marzo Veronese et al., Structural Mimicry and Enhanced Immunogenicity of Peptide Epitopes Displayed on Filamentous Bacteriophage, J. Mol. Biol., 243:167-172 (1994).
Hogrefe et al., Cloning in a bacteriophage lambda vector for the display of binding proteins on filamentous phage, Gene, 137:85-91 (1993).
Homyk et al., Deletion Analysis of Two Nonessential Regions of the T4 Genome, Virology 61:505-523 (1974).
Hong et al., An expression-packaging-processing vector which selects and maintains 7-kb DNA inserts Gene 136:193-198 (1993).
Iannolo et al., Modifying Filamentous Phage Capsid: Limits in the Size of the Major Capsid Protein, J. Mol. Biol., 248:835-844 (1995).
Ishii et al., The Two Dispensable Structural Proteins (SOC and hoc) of the T4 Phage Capsid; their Purification and Properties, . . . , J. Mol. Biol. 109:487-514 (1977).
Ishii et al., Molecular Organization of the Shell of the . . . , J. Mol. Biol., 97:655-660 (1975).
Ishii et al., Binding of the Structural Protein to the Head Shell of Bacteriophage T4, J. Mol. Biol. 120:533-544 (1978).
Jespers et al., Surface Expression and Ligand-Based Selection of cDNAs Fused to Filamentous Phage Gene VI, Bio Technology, 13:378-382 (1995).
Kishchenko et al., Structure of a Foreign Peptide Displayed on the Surface of Bacteriophage M13, J. Mol. Biol., 241:208-213 (1994).
Kitamura et al., Primary structure, gene organization and polypeptide expression of poliovirus RNA, Nature 291:547-553 (1981).
Krchnak et al., Bifunctional scaffolds as templates for synthetic combinatorial libraries, Mol. Diversity, 1:177-182 (1995).

(Continued)

*Primary Examiner*—Jeffrey S. Parkin
*Assistant Examiner*—Lisa V Cook
(74) *Attorney, Agent, or Firm*—Needle & Rosenberg

(57) ABSTRACT

Disclosed is a phage display system in which the molecules to be displayed (i.e., molecules of interest) are bound to dispensable capsid polypeptides such as SOC (small outer capsid) and HOC (highly antigenic outer capsid) polypeptides that are, in turn, bound to a surface lattice protein, such as those on the surface of a virion or polyhead. Also disclosed are methods of displaying a molecule of interest, methods of immunizing a patient by administering a displayed antigen, and methods of treating a patient who has a disorder associated with aberrent expression or activity of a biological molecule. In the latter instance, the method includes administering a displayed polypeptide, such as an immunoglobulin molecule or an enzyme, that is capable of specifically interacting with the aberrent biological molecule.

7 Claims, 11 Drawing Sheets

OTHER PUBLICATIONS

Laman et al., Variant-Specific Monoclonal and Group-Specific Polyclonal Human Immunodeficiency Virus Type 1 Neutralizing Antibodies . . . , J. Virol., 66:1823-1831 (1992).

Li et al., Poliovirus Neutralization by Antibodies to Internal Epitopes of VP4 and VP1 Results from Reversible Exposure . . . , J. Virology, 68:3965-3970 (1994).

Marks et al., Molecular Evolution of Proteins on Filamentous Phage, J. Biol. Chem., 267:16007-16010 (1992).

McCafferty et al., Phage antibodies: filamentous phage displaying antibody variable domains, nature 348:552-554 (1990).

Orum et al., Efficient method for constructing comprehensive murine Fab antibody libraries displayed on phage, Nucl. Acids Res., 21:4491-4498 (1993).

Parmley et al., Antibody-selectable filamentous fd phage vectors: affinity purification of target genes, Gene 73:305-318 (1988).

Perham et al., Engineering a peptide epitope display system on filamentous bacteriophage, FEMS Microbiol. Rev., 17:25-31 (1995).

Ren et al., Phage display of intact domains at high copy number: A system based on SOC, the small outer capsid . . . , Protein Science 5:1833-1843 (1996).

Ross et al., Assembly-dependent Conformational Changes in a Viral Capsid Protein, J. Mol. Biol. 183:353-364 (1985).

Skerra et al., Secretion and in vivo folding of the Fab fragment of the antibody McPC603 . . . , Protein Engineering, 4:971-979 (1991).

Smith et al., A ribonuclease S-peptide antagonist discovered with a bacteriophage display library, Gene, 128:37-42 (1993).

Smith et al., Filamentous Fusion Phage: Novel Expression Vectors That Display Cloned Antigens . . . , Science, 228:1315-1317 (1985).

Steven et al., The Maturation-Dependent Conformational Change of the Major Capsid Protein of . . . , Biochemistry, 29:5556-5561 (1990).

Steven et al., Structure of T4 Polyheads, J. Mol. Biology, 106:187-221 (1976).

Studier et al., Use of T7 RNA Polymerase to Direct Expression of Cloned Genes, Methods in Enzymology, 185:60-89 (1990).

Van der Werf et al., Localization of a poliovirus type 1 neutralization epitope in viral capsid polypeptide VP1, Proc. Natl. Acad. Sci., 80:5080-5084 (1983).

Williamson et al., Human monoclonal antibodies against a plethora of viral pathogens from single combinatorial libraries, Proc. Natl. Acad. Sci., 90:4141-4145 (1993).

Wu et al., Reiterated Gene Amplifications at Specific Short Homology Sequences in Phage T4 Produce Hp17 Mutants, J. Mol. Biol., 218:705-721 (1991).

* cited by examiner

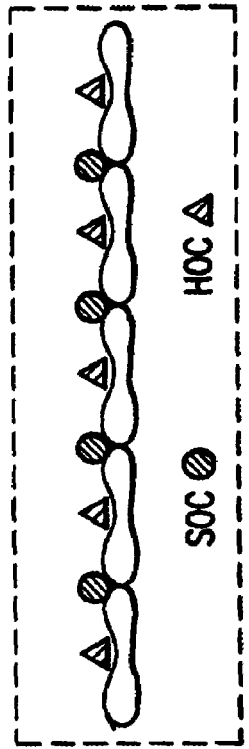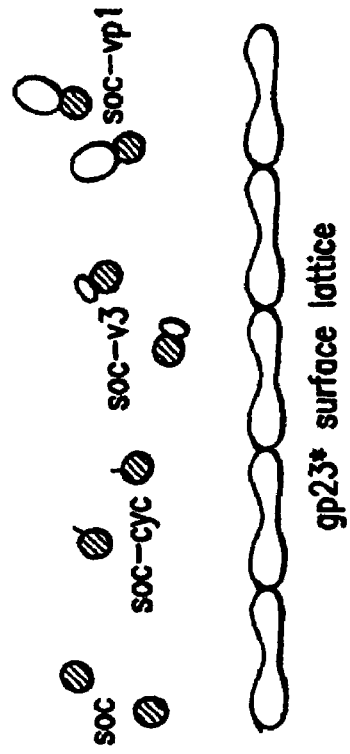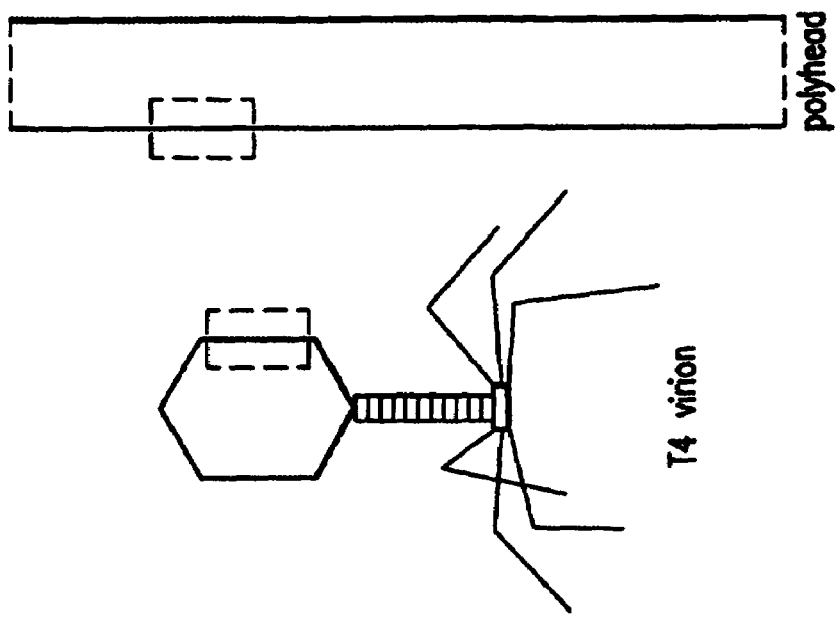

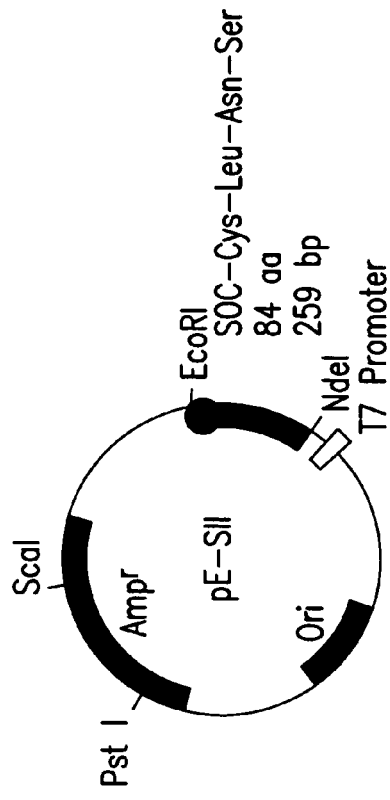
FIG.2A-b
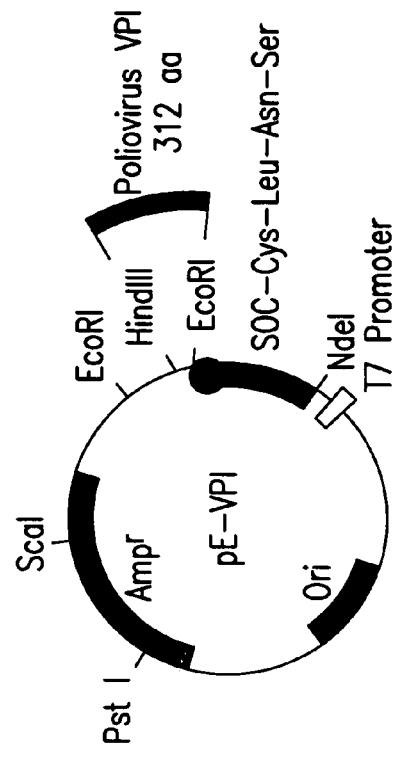
FIG.2A-d
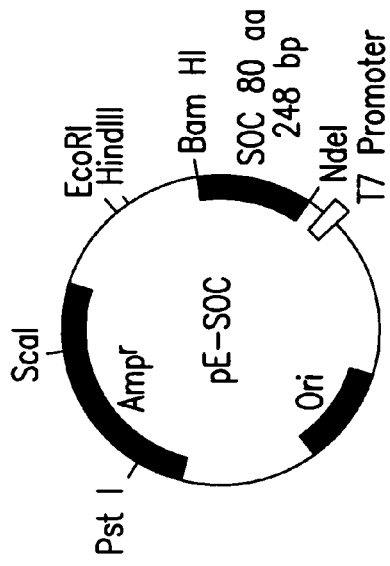
FIG.2A-a
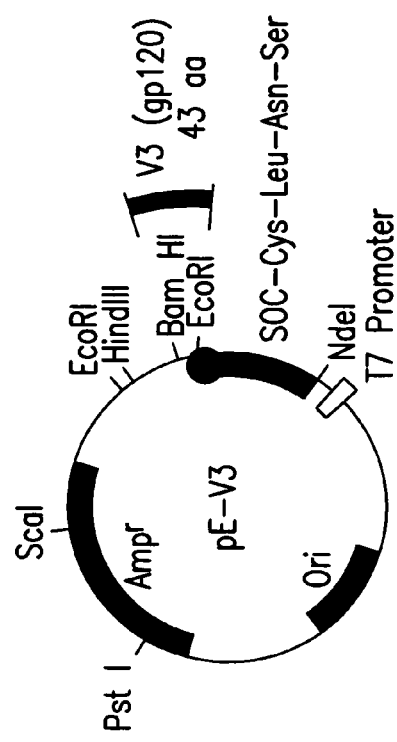
FIG.2A-c

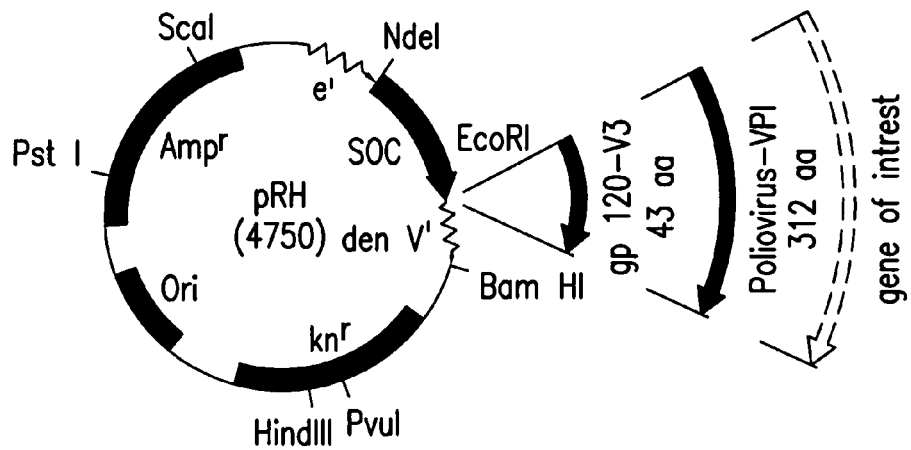
FIG.2B-a
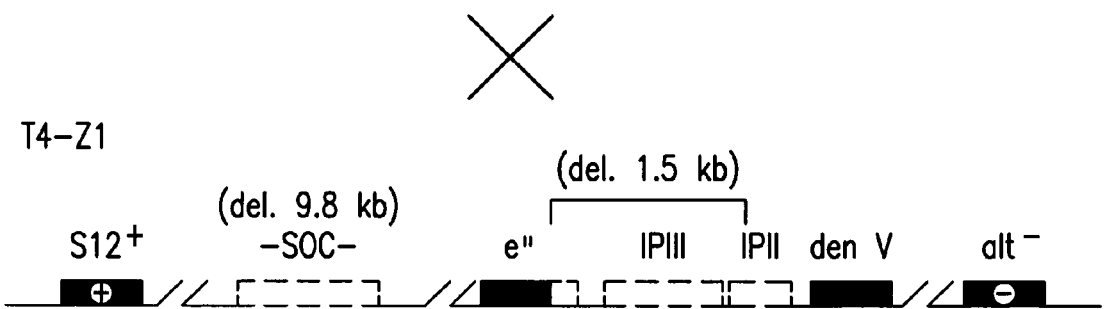
FIG.2B-b
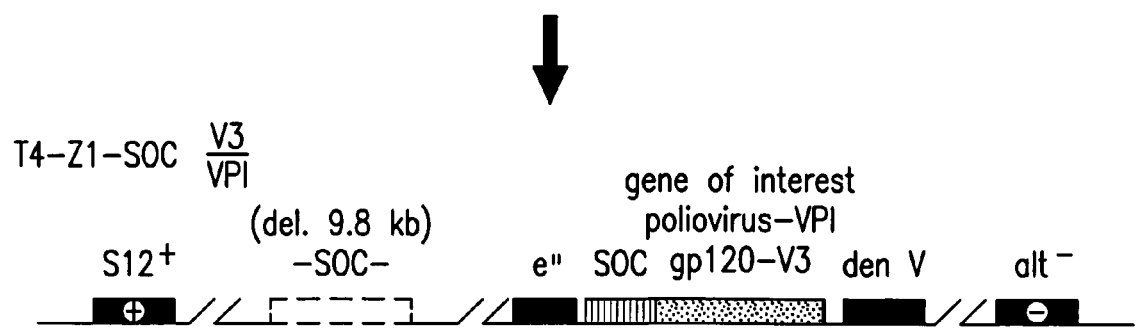
FIG.2B-c

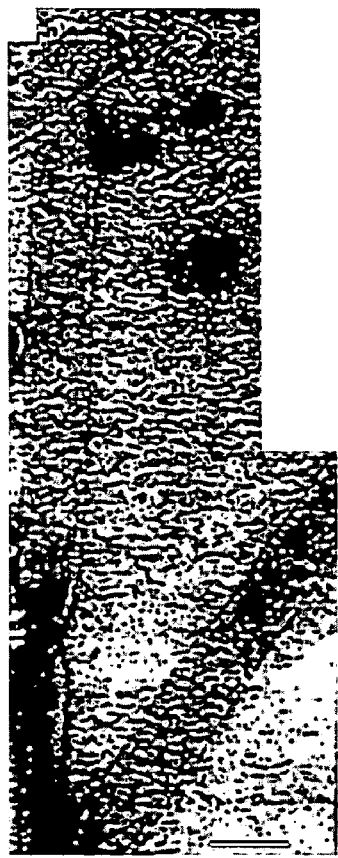
FIG.8A
FIG.8B
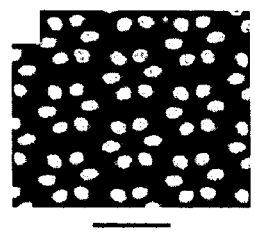
FIG.8D
FIG.8C
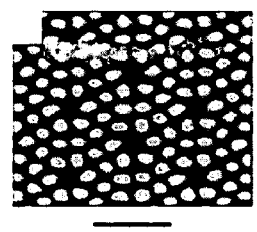
FIG.8E

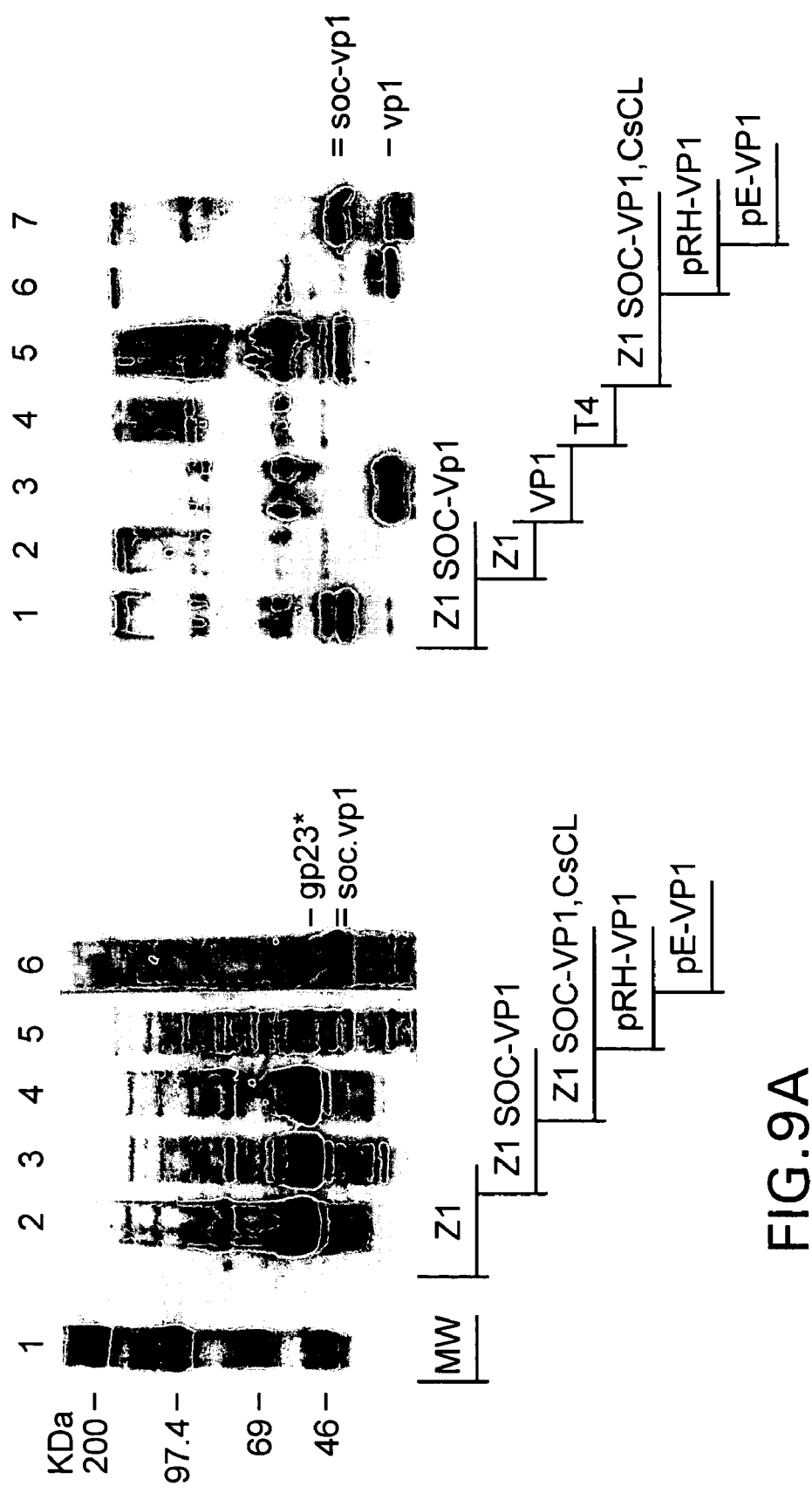

PHAGE DISPLAY OF INTACT DOMAINS AT HIGH COPY NUMBER

The work described herein was carried out, in part, at the National Institute of Arthritis and Musculoskeletal and Skin Diseases, National Institutes of Health. The government therefore may have certain rights in the invention.

BACKGROUND OF THE INVENTION

The field of the invention is phage display.

Filamentous phage-based display systems (as described, for example, in Smith, *Science* 228:1315–1317, 1985) have found widespread use in molecular biology, including many immunologic applications such as antigen presentation and the immuno-isolation of desired recombinants by "biopanning" (Marks et al., *J. Biol. Chem.* 267:16007–16010, 1992; Smith et al., *Gene* 128:37–42, 1993; Williamson et al., *Proc. Natl. Acad. Sci. USA*, 90:4141–4145, 1993). However, with filamentous phages, peptides that may be displayed from the major coat protein are limited in size to 6–10 amino acid residues (Kishchenko et al., *J. Mol. Biol.* 241:208–213, 1994; Iannolo et al., *J. Mol. Biol.* 248:835–844, 1995), although somewhat longer peptides can be displayed by co-assembly with the wild-type coat protein (Perhan et al., *FEMS Microbiol. Rev.* 17:25–31, 1995). Full-length polypeptides can be displayed on minor phage proteins, but only at very low copy number (Parmley and Smith, *Gene* 73:305–318, 1988). Moreover, the requirement that the fusion protein should pass through the secretion system of *Escherichia coli* may pose problems of toxicity for the host, or for correct folding of the displayed protein (Skerra and Plückthun, *Protein Eng.* 4:971–979, 1991).

SUMMARY OF THE INVENTION

Described herein is a phage display system in which the molecules to be displayed (i.e., molecules of interest) are bound to dispensable capsid polypeptides such as SOC (small outer capsid) and HOC (highly antigenic outer capsid) polypeptides that are, in turn, bound to a surface lattice protein, such as those on the surface of a virion or polyhead. Polyheads are tubular capsid variants, and their formation is described below. Also described below are various ways in which a molecule of interest can be displayed. For example, a chimeric polypeptide that includes a dispensable polypeptide and a polypeptide of interest can be expressed in *Escherichia coli*, purified, and then bound in vitro to separately isolated surface lattice proteins. The surface lattice proteins can be those on the surface of a capsid or polyhead from which the wild type dispensable polypeptides have been deleted. Similarly, a chimera that contains a dispensable polypeptide and a synthetic molecule of interest can be prepared in vitro and bound to surface lattice proteins. In another embodiment, a positive selection vector forces integration of a gene that encodes a dispensable polypeptide and a polypeptide of interest into the genome of a phage from which the wild type dispensable polypeptide is deleted. For example, a modified soc gene can be integrated into a soc-deleted T4 genome, leading to in vivo binding of the display molecule on progeny virions. More than one type of dispensable polypeptide can be used as part of the chimera for displaying one or more molecules of interest. For example the surface lattice proteins of a phage may be bound to a chimera that contains SOC and a chimera that contains HOC.

The display system has been successfully demonstrated for three molecules of interest that vary in their length and character: (1) a tetrapeptide; (2) the 43 amino acid residue V3 loop domain of gp120, the human immunodeficiency virus type-1 (HIV-1) envelope glycoprotein; and (3) poliovirus VP1 capsid protein (312 residues).

The display system of the invention is capable of presenting approximately 1,000 copies or more of the displayed molecule of interest per capsid and 10,000 copies or more per polyhead of V3-sized domains. Appropriate binding between the fusion protein and the surface lattice was apparent in averaged electron micrographs of polyheads. Furthermore, phage displaying the V3 loop domain of gp120 were highly antigenic in mice and produced antibodies reactive with native gp120. In addition, phage displaying SOC-VP1 were isolated from a $1:10^6$ mixture by two cycles of a simple biopanning procedure, indicating that proteins of at least 35 kDa may be accommodated. Therefore, the system described herein can be used in numerous immunologic applications, including treatments that rely on antigen or antibody persentation, and in the isolation of various polypeptides and other pharmacophores. The fact that the molecules of interest are displayed at high copy number greatly facilitates these applications, and the fact that the molecules of interest are displayed on surface lattice proteins that form regular arrays allows analysis of their structure as well.

BRIEF DESCRIPTION OF THE DRAWING

FIGS. 1A–1D are a series of schematic diagrams illustrating the principle of the novel display system described herein. A segment of the surface lattice (dashed boxes) of a virion (illustrated on the left of FIG. 1A) and a polyhead (illustrated on the right of FIG. 1A) is shown in FIG. 1B. The display platform (in this case, a SOC-less capsid or polyhead) and SOC (small outer capsid) and chimeras that contain SOC are shown in FIG. 1C. Chimeric proteins are shown bound to the display platform in FIG. 1D. The viability of the phage display system is demonstrated for three polypeptides, which are illustrated in FIG. 1C and FIG. 1D as soc-cys, where cys=Cys-Leu-Asn-Ser, as soc-v3, where SOC is fused to a 47-residue polypeptide, and SOC-vp1, where SOC is fused to a 312-residue polypeptide.

FIGS. 2A–2B are schematic diagrams of vectors constructed as described herein and a region of the T4–Z1 phage that has been altered by homologous recombination in a phage-plasmid cross. The expression vectors shown in FIG. 2A are: pE-SOC, into which a 248 base pair SOC-encoding sequence has been inserted (panel i); pE-S11, into which a 259 base pair sequence encoding SOC and the tetrapeptide Cys-Leu-Asn-Ser has been inserted (panel ii); pE-V3, which, in addition to the SOC-tetrapeptide sequence, encodes 43 amino acids of V3 (gp120) (panel iii); and pE-VP1, which, in addition to the SOC-tetrapeptide sequence, encodes 312 amino acids of the poliovirus capsid protein, VP1 (panel iv). FIG. 2B illustrates pRH, a phage integration plasmid that contains a portion of the phage T4 lysozyme gene e' at the 5' end of the modified soc gene, and a portion of the 3' denV' gene of T4 (panel i). Homologous recombination with the T4–Z1 phage, which is deleted for genes soc, IPIII, IPII, and part of e", is shown in panel ii. Following recombination, which forms an intact gene e and transfers the modified soc gene into the phage genome, an egg white lysozyme-independent phage plaque selects for the soc gene (panel iii).

FIGS. 8A–8E are electron micrographs of T4 polyheads (cleaved/expanded type) after complementation with SOC-V3 (FIG. 8A; Bar=100 nm), an individual polyhead at higher magnification (FIG. 8B, inset within FIG. 8A; Bar=50 nm), computer-filtered image of the surface lattice at ~3 nm resolution (FIG. 8C; Bar=15 nm), the undecorated gp23* surface lattice (FIG. 8D), and the lattice decorated with wild-type SOC (FIG. 8E; reproduced from Ross et al., J. Mol. Biol. 183:353–364, 1985; Bar=15 nm). Triplets of SOC binding sites surround the points of local three-fold symmetry in the hexagonal surface lattice (FIG. 8E). In the SOC-V3 binding experiment (FIG. 8C), these sites are occupied by stain-excluding units that are somewhat larger than those observed with wild-type SOC, consistent with the greater size of the SOC-V3 fusion protein. Thus, occupancy of the SOC sites by SOC-V3 molecules is complete or close to it, because the peak density above background of the SOC-V3-related units in FIG. 8C is, on average, 10–15% higher than for the gp23* related units.

FIGS. 9A and 9B are a pair of photographs of an SDS-polyacrylamide gel, stained to reveal protein (FIG. 9A), and a Western blot (FIG. 9B) of the same samples. Molecular weight standards are shown in lane 1 of FIG. 9A. The samples examined in FIG. 9A are as follows; CsC1-purified virion of the recombination phage Z1 (Z1; lane 2), the soc-vpl Z1 integrant, purified by high-speed centrifugation (Z1 SOC-VP1; lane 3), the soc-vpl Z1 integrant, purified by high-speed centrifugation and additionally by CsC1 gradient centrifugation (Z1 SOC-VP1, CsC1; lane 4), products of the expression vector pE-VP1 (pE-VP1; lane 6) and the recombination ventor pRH-VP1 (pRH-VP1; lane 5) have the expected apparent molecular weight of 43 kDa. The Western blot shown in FIG. 9B is stained with anti-VP1 antiserum. The samples are as described in FIG. 9A and, in addition, include purified poliovirus (lane 3) and the same amount of T4 (lane 4) as Z1 and Z1-soc-vpl phages (lanes 1, 2, 5), as a negative control.

In FIG. 10A, molecular weight standards are shown in lane 1. DNA derived from the soc gene (259 bp) can be detected in expression vector PE-VP1 (lane 3), T4 (lane 4), and Z1-soc-vp1 integrant (lane 6), but not in delsoc (lane 5), Z1 (before recombination; lane 10), or buffer used for single plaque test (lane 2). C1, C2 and C3 (shown in lanes 9, 8, and 7, respectively) are samples obtained following successive cycles of biopanning. The soc gene can be detected in a mixture of phages arising from the second cycle of precipitation followed by growth. In FIG. 10B, the same phage samples are assayed by Western blotting with the anti-VP1 antibody.

DETAILED DESCRIPTION

Figure 3:
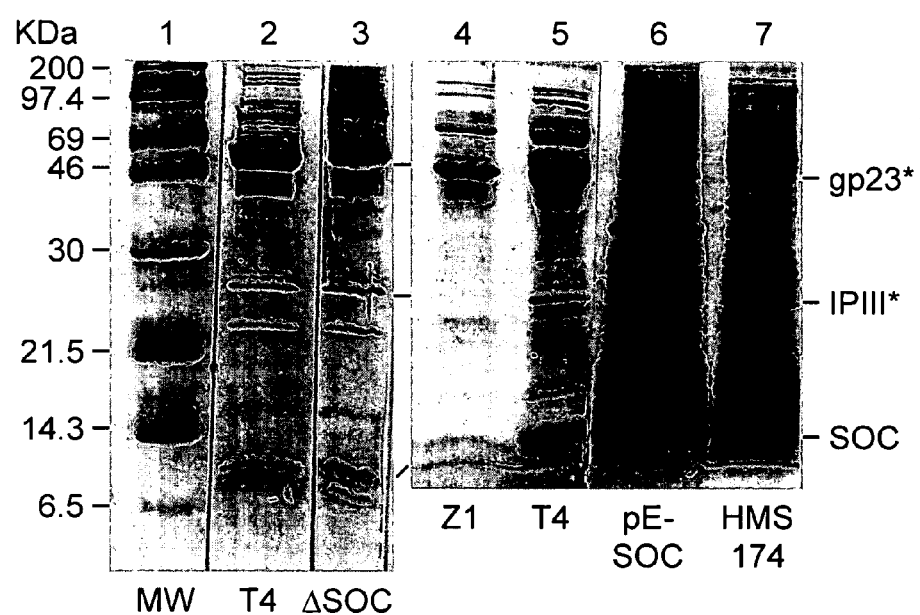
FIG. 3 is a photograph of an SDS-polyacrylamide gel, stained to reveal protein. Lane 1 contains molecular weight standards; lanes 2 and 5 contain wild-type T4 phage; lane 3 contains soc-deleted T4 phage; lane 4 contains the integration phage Z1, which lacks viral proteins SOC, IPIII, IPII, and ALT; lane 6 contains SOC expressed from HMS174 bacteria containing the plasmid pE-SOC; and lane 7 contains lysates of HMS174 bacteria that lack the plasmid.
Figure 4B:
FIGS. 4A and 4B are a pair of photographs of an SDS-polyacrylamide gel, stained to reveal protein (FIG. 4A) and a Western blot (FIG. 4B) of the same samples. The samples analyzed by SDS-PAGE in FIG. 4A include: E. coli overexpressing SOC-V3 (~14 kDa, pEV3, lane 2); recombination phage lacking SOC and IpIII (Z1, lane 3); phage purified by high-speed centrifugation followed by CsC1 density gradient centrifugation (Z1 SOC-V3, CsC1, lane 4) or by the first step only (Z1 SOC-V3; lane 5); and wild-type T4 phage (T4, lane 6). Molecular weight standards were run in lane 1. The same samples were examined following Western blotting using antiserum against gp120 of HIV-1 (FIG. 4B).
Figure 4A:
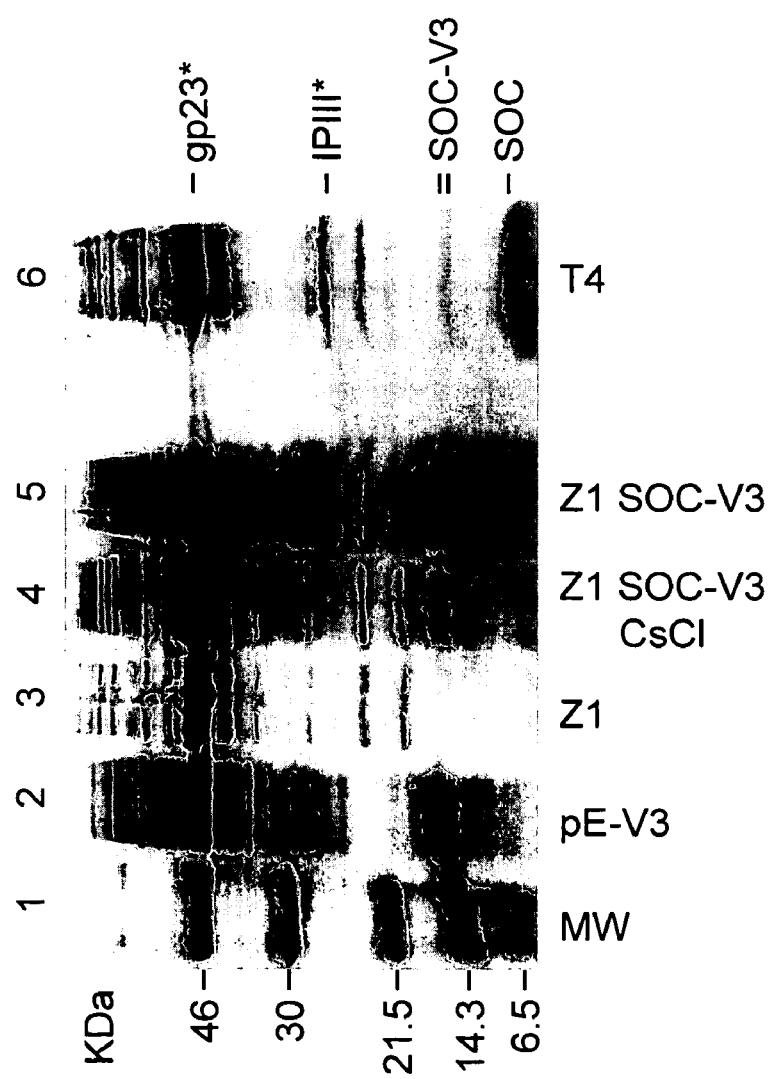

The invention features a system for displaying molecules of interest. The displayed molecules are bound to a dispensable polypeptide that can, in turn, bind a protein that is part of the lattice found on the surface of a virion or polyhead.

The term chimera is used herein to describe the entity that is formed when a display molecule is bound to a dispensible polypeptide; when the display molecule is also a polypeptide, the chimera is referred to as a chimeric polypeptide. The terms "protein" and "polypeptide" are used herein to refer to any chain of two or more amino acid residues, regardless of the length of the chain or the presence or absence of post-translational modifications such as glycosylation or phosphorylation.

The chimera can consist of numerous types of display molecules and dispensable polypeptides. For example, the dispensable polypeptides can be a small outer capsid (SOC) polypeptide or a highly antigenic outer capsid (HOC) polypeptide, such as those expressed on the surface of the bacteriophage T4. The dispensable polypeptide used according to the method of the invention need not be identical, either in length or sequence, to a wild-type dispensable polypeptide. It may, for example, contain mutations including substitutions, deletions, and/or additions of amino acid residues, provided these mutations do not destroy the ability of the dispensable polypeptide to bind a display molecule and a surface lattice protein.

The T4 SOC polypeptide and the related polypeptide, HOC, have a number of features that allow them to function as vehicles for displaying molecules of interest. Any polypeptide that has one or more of these features may, therefore, be useful as a dispensable polypeptide in various embodiments of the present invention. These features include their arrangement on the surface of a virion or polyhead, the level at which they are expressed, their ability to withstand particular conditions of temperature and pH, and the degree to which the dispensable polypeptide is required for capsid morphogenesis.

SOC is a small protein (9 kDa) that is nonessential for T4 capsid morphogenesis (Ishii and Yanagida, *J. Mol. Biol.* 97:655–660, 1975) but, if available, binds with high affinity to numerous sites on the outer surface of a mature capsid (Aebi et al., *J. Mol. Biol.* 110:687–698, 1977; Ishii et al., *J. Mol. Biol.* 120:533–544, 1978) or a polyhead (Steven et al., *J. Mol. Biol.* 106:187–221, 1976). Thus, a chimera can be assembled without passage through a secretory pathway. In addition, because triplets of SOC binding sites are spaced ~7 nm apart, and within a triplet, the three sites are ~4 nm apart (see FIG. 8d), steric blocking should not occur unless extremely large molecules are displayed. In such cases, one would still anticipate successful display at reduced occupancy, e.g., when one copy of the display protein is bound at each triplet of SOC binding sites. If necessary, the expression level of dispensable polypeptides, such as SOC, can be controlled by introducing suppressible termination codons adjacent to the initiation codon of the gene encoding the dispensable polypeptide.

Dispensable polypeptides also allow many copies of a molecule of interest to be displayed. For example, SOC binds in equimolar stoichiometry to the major capsid protein gp23*, which is present in approximately 1,000 copies per capsid (a capsid is commonly believed to contain 960 copies of gp23*), or more than 10,000 copies per polyhead. Triplets of SOC binding sites surround the local threefold symmetry axes on the hexagonal gp23* surface lattice (Aebi et al., *J. Supramol. Struct.* 5:475–495, 1976). Thus, approximately $10^3$–$10^4$ or more densely packed copies of a molecule of interest can be displayed on a surface lattice such as the outer surface of a single phage or polyhead (FIG. 1).

Moreover, dispensable polypeptides, such as SOC and HOC, that bind the surface lattice proteins can be restored readily to full capsid-binding activity after denaturation in guanidine hydrochloride (Ishii and Yanagida, *J. Mol. Biol.* 109:487–514, 1977) or by heating. These features indicate that it should be possible to retrieve chimeras that consist of the molecule of interest and a dispensable polypeptide from inclusion bodies in a state competent to bind to a surface lattice protein. In addition, because SOC stabilizes phage at high pH (Ishii et al., *J. Mol. Biol.* 108:487–514, 1978) or elevated temperatures (Ross et al., *J. Mol. Biol.* 183:353–364, 1985), it should be possible to select for phage displaying chimeras that contain SOC, or another dispensable polypeptide that stabilizes phage under extreme conditions, by exposing them to these conditions, which non-SOC bearing phage cannot tolerate.

The display molecule can be virtually any molecule that can be bound to a dispensable polypeptide. Thus, a display molecule can be a naturally occurring biological molecule that is obtained either from a natural source, such as a plant or an animal tissue, or from a synthetic process. Alternatively, the display molecule can be inorganic.

A biological molecule can be displayed in a form that mimics the form in which it is expressed in nature. For example, a biological molecule can be the same in size and have the same secondary or tertiary structure as it is thought to have in a naturally occurring plant or animal. Alternatively, a biological molecule can be displayed in a form that is different from the form in which it is found in nature. For example, a fragment of a biological molecule can be displayed. In addition, either the full length molecule or a fragment thereof can be altered. For example, in the event the display molecule is a polypeptide, it can be altered by mutation, i.e., one or more amino acid residues can be substituted with another amino acid, or deleted. Alternatively, or in addition, the mutant can contain additional amino acid residues. The wild-type or mutant biological molecule being displayed can be further altered by, for example, phosphorylation or glycosylation, and can be bound to additional moieties including other naturally occurring molecules and inorganic substances. Display molecules that are fragmented or otherwise altered as described above may be referred to as derivatives or analogs of a naturally occurring molecule.

Biological molecules that can be displayed include polypeptides, such as those that function as hormones, enzymes, neurotransmitters, growth factors, cytokines, cell surface adhesion molecules, receptors, antigens, or antibodies. Carbohydrates that are present on glycoproteins can also be displayed. As described above, fragments of biological molecules can be displayed. For example, antibody fragments (e.g., Fab, Fab', F(ab')$_2$), and single-chain antibodies can be displayed.

Structurally, the simplest antibody (IgG) comprises four polypeptide chains, two heavy (H) chains and two light (L) chains that are inter-connected by disulphide bonds. The light chains exist in two distinct forms called kappa (K) and lambda (λ). Each of the H and L chains have a constant region (C) and a variable region (V), and each is organized in a series of domains. The light chains have two domains, one that corresponds to the C region and one that corresponds to the V region. The heavy chains have four domains, one that corresponds to the V region and three domains (1, 2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognizing an antigen and providing an antigen binding site (ABS).

The V region is further defined as having three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation, and selection.

It has been shown that the function of binding antigens can be performed by fragments of a whole antibody. Examples of binding fragments are (i) the Fab fragment consisting of the VL, VH, CL, and CH1 domains; (ii) the Fd fragment consisting of the VH and CH1 domains; (iii) the Fv fragment consisting of the VL and VH domains of a single arm of an antibody; (iv) the dAb fragment (Ward et al., *Nature* 341:544–546, 1989) which consists of a Vh domain; (v) isolated CDR regions; and (vi) F(ab')2 fragments, a bivalent fragment comprising two Fab fragments linked by a disulfide bridge at the hinge region.

Although the two domains of the Fv fragment are coded for by separate genes, it is possible to make a synthetic linker that enables them to be made as a single protein chain (known as single chain Fv (scFv); Bird et al., *Science*

242:423–426, 1988; Huston et al., *Proc. Natl. Acad. Sci. USA* 85:5879–5883, 1988) by recombinant methods. These scFv fragments were assembled from genes from monoclonals that had been previously isolated.

An antibody displayed according to the method of the invention can be a "neutralizing" antibody that interferes with one or more of the biological activities of the antigen to which it binds. The activities of the antigen can be reduced by at least 50%, more preferably by at least 70%, and most preferably by at least 90% or more.

Like antibodies, many of the molecules that can be displayed constitute a first member of a binding pair because they specifically bind a second molecule. Examples of specific binding pairs include antigen-antibody, antigen-antibody fragment, hapten-antibody, ligand-receptor (for example, hormone—hormone receptor, neurotransmitter—neurotransmitter receptor, growth factor-growth factor receptor, cytokine—cytokine receptor), enzyme-substrate, carbohydrate-lectin, immunoglobulin-protein A, and molecularly imprinted polymer-imprinted compound; in each example, either the first or the second type of molecule listed could be designated as the first member of the binding pair.

In addition to biological molecules, inorganic or synthetic molecules can be displayed. It is well within the abilities of skilled chemists to form a bond between a dispensable polypeptide and an inorganic or synthetic molecule. For example, aromatic hydroxy acids can be bound to the amino terminal group of the most N-terminal amino acid of the dispensable polypeptide, and alcohols can be bound to phenolic hydroxyl groups within the dispensable polypeptide by etherification. If the dispensable polypeptide does not contain an accessible hydroxyl group, one may be provided by adding a linker, such as one or more serine, threonine, or tyrosine residues, to the dispensable polypeptide. Small molecules, such as the aromatic hydroxy acids and alcohols described above can be displayed in randomized combinations, with or without amino acids. Thus, the chimeras of the invention can be used to generate a combinatorial library of potential pharmacophores. For specific examples of aromatic hydroxy acids, alcohols, and amino acids, persons of skill in the art may consult Krchnak et al. (*Mol. Diversity* 1:177–182, 1995), a publication which describes the production of a small-molecule synthetic combinatorial library that features potential pharmacophores attached to a variety of small cyclic scaffolds. The chimeras of the present invention do not impede assembly of a display platform.

The virions that can be used in the present invention include double stranded DNA phages, such as T4, that encode dispensable accessory proteins such as the dispensable proteins SOC and HOC described herein. Other virions that could be used include phage λ and T7. The coats of most bacteriophage are highly ordered. For example, filamentous phage can be described and characterized by the presence of a helical lattice, while isometric phage are so known by an icosahedral lattice. Each monomer of each major coat protein sits on a lattice point and makes defined interactions with each of its neighbors. Proteins that fit into the lattice by making some, but not all, of the normal lattice contacts are likely to destabilize the virion by (a) aborting formation of the virion, (b) making the virion unstable, or (c) leaving gaps in the virion so that the nucleic acid is not protected. Thus, in genetically altered bacteriophage, it is important to retain the expression of proteins, or fragments thereof, that stabilize the surface lattice. The surface lattice protein of bacteriophage T4, gp23*, which is described further below, can be entirely unaltered in the practice of the instant invention.

When the invention is practiced by integrating a nucleic acid molecule that encodes a dispensable polypeptide and a polypeptide of interest (as the display molecule) into the genome of the phage, the phage must in some way allow introduction of the nucleic acid molecule. It must, for example, tolerate additional genetic material, or have genetic material that can be replaced by a nucleic acid molecule that encodes a dispensable polypeptide and a polypeptide of interest. Large tracts of the T4 genome are non-essential. Thus, large nucleic acid molecules, such as those containing all or part of soc, can readily be accommodated. Furthermore, the phage must be capable of packaging the genome after accepting such a nucleic acid molecule, and the display of the chimeric polypeptide on the phage surface must not disrupt the structure of the phage in a way that interferes with propagation of the phage. Those of ordinary skill can readily determine whether a phage is suitable for use in the context of the present invention without resort to undue experimentation.

Accordingly, in one embodiment, the invention features a method of displaying a polypeptide of interest on the surface of a virion from which all or part of the nucleic acid encoding a wild type dispensable polypeptide has been deleted. The method can be carried out by integrating into the genome of the virion a chimeric nucleic acid molecule that includes a nucleic acid sequence that encodes a dispensable polypeptide that binds to a surface lattice protein of the virion and a nucleic acid sequence that encodes the polypeptide of interest. Alternatively, the chimera can be separately expressed (for example, by a biological cell), or otherwise formed (for example, by a chemical reaction carried out in vitro), and bound to capsids or polyheads from which a dispensable polypeptide has been deleted. The means to carry out these processes (i.e., the construction of a chimera and the process of binding a chimera to a capsid or polyhead) are well within the abilities of those of ordinary skill in the art.

Methods of integrating a nucleic acid molecule that encodes a chimeric polypeptide (that will be displayed on the surface of the phage) into the genome of the phage are well known in the art and include, for example, homologous recombination (for example, see Winona et al. *J. Bacteriol.* 161:219–221, 1985). To perform homologous recombination, the nucleic acid molecule to be integrated is typically carried within a recombinant vector, such as a plasmid.

The recombinant vectors of the present invention include those with a plasmid vector backbone and a nucleic acid molecule that encodes a chimeric polypeptide. The chimeric polypeptide includes a dispensable polypeptide and a polypeptide of interest, as described above. To facilitate insertion of the exogenous nucleic acid molecule, the plasmid can also contain nucleic acid sequence that is complementary to the sequence in the vicinity of the desired site of insertion. For example, to insert a chimeric nucleic acid molecule into the site of the T4 endogenous soc gene, the plasmid used can contain a nucleic acid sequence encoding all or part of a T4 lysozyme gene (e') and a T4 den V' gene.

The recombinant vectors can also include a promoter sequence that is operably linked to the nucleic acid molecule encoding the chimeric polypeptide. Promoters, including the IPIII promoter described below, are well known in the art and can readily be selected by those of skill in the art. Typically, the DNA segment encoding the chimeric polypeptide is positioned downstream from the promoter sequence. The vector can also contain a marker or reporter gene, or a gene that allows for selection, such as a gene that confers antibiotic resistance.

Bacteriophages can be used in the methods described below because there is little or no enzymatic activity associated with intact mature phage, and the genes are inactive outside of a bacterial host, rendering the mature phage particles metabolically inert.

Thus, the invention features a method of immunizing a mammal by administration of an antigenic composition that includes a surface lattice protein that is bound to a chimeric polypeptide. In this instance, the chimeric polypeptide would contain an antigenic polypeptide and a dispensable polypeptide that binds to the surface lattice protein. A polypeptide is consider antigenic if it is able to specifically bind to (i.e., immunoreact with) an antibody and form an immunocomplex. The site on the antigen with which the antibody binds is referred to as an antigenic determinant or epitope.

The antigenic polypeptide can be, for example, a bacterial, viral, parasitic, fungal, or tumor antigen. Alternatively, self-antigens can illicit an immune response and can be used in the immunization method described above. Examples of viral antigens include antigens derived from viruses such as the hepatitis B virus (HBV), human immunodeficiency virus (HIV), influenza A virus, Epstein Barr virus (EBV), herpes simplex virus (HSV), respiratory syncytial virus (RSV), human cytomegalovirus (HCMV), varicella zoster virus (VZV), and measles virus. Persons of ordinary skill in the art are readily able to determine the antigenicity of a polypeptide, and thus, the suitability of that polypeptide for use in a method of the invention.

In addition to immunization, the display system described herein can be used in methods of treatment. For example, a mammal having a disorder associated with aberrent expression or activity of a biological molecule can be treated by administration of a therapeutic composition that includes a surface lattice protein that is bound to a chimeric polypeptide. In this embodiment, the chimeric polypeptide can include a dispensable polypeptide that binds a surface lattice protein and an immunoglobulin molecule that binds to the biological molecule that is overly expressed or overly active. The activity of a biological molecule, for example a molecule that is overly expressed or overly active in a patient, can also be altered by administering to the patient a chimera that contains a dispensable polypeptide and an enzyme that specifically interacts with the biological molecule. The enzyme displayed may be an intact or full-length enzyme or a fragment thereof that retains enzymatic activity. Examples of enzymes that can profitably be displayed include hemagglutinase and anti-clotting enzymes. Persons of ordinary skill in the art are readily able to determine whether a disease, disorder, or other condition can be treated by administration of a particular enzyme on the display platform described herein. In addition to the use of display molecules in clinical treatment, the method of the invention can be used to generate novel reagents for use in biotechnological pursuits which have been hampered by the unavailability of stable, multimeric copies of rare or expensive enzymes.

Toxicity and therapeutic efficacy of a given compound can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

It is well known in the medical arts that dosages for any one patient depend on many factors, including the general health, sex, weight, body surface area, and age of the patient, as well as the particular compound to be administered, the time and route of administration, and other drugs being administered concurrently.

Dosages for the therapeutic compositions of the instant invention will vary; a dosage of a displayed molecule could range from 1 μg to 1 mg per application. For example, 10 μg to 100 μg can be administered. This dosage can be given once or on numerous occassions, as required. Determination of the correct dosage within a given therapeutic regime is well within the abilities of one of ordinary skill in the art of pharmacology. It is possible that an additional advantage of the invention described herein is that it may allow treatment with less antigen than has previously been required.

The compositions of matter used in the methods described above are also considered within the scope of the invention. These compositions include therapeutic compositions (e.g., those containing chimeras or chimeric polypeptides, both of which include a dispensable polypeptide), phage that contain a chimeric nucleic acid molecule encoding a dispensable polypeptide and a polypeptide of interest, polyheads that are bound by chimeras or chimeric polypeptides, the chimeric nucleic acid molecules themselves, and the polypeptides they encode.

Pharmaceutical compositions for use in accordance with the present invention can be formulated in a conventional manner using one or more physiologically acceptable carriers or excipients. Thus, the compounds and their physiologically acceptable salts and solvates may be formulated for administration by inhalation or insufflation (either through the mouth or the nose), or for oral, buccal, subcutaneous, intraperitoneal, intravenous, intraarterial, intracerebral, or intramuscular administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The therapeutic compositions of the invention can also contain a carrier or excipient, many of which are known to persons of skill in the art. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. Methods for making such formulations are well known and can be found in, for example, "Remington's Pharmaceutical Sciences." It is likely that a commonly used route of administration will be intravenous.

Virions and polyheads have complementary advantages as display platforms. For example, phage express and bind chimeric polypeptide directly in vivo, obviating the need for a step in which the chimeras are separately purified, and might be propagated in situ in an immunized host. Polyheads, however, are advantageous because they have an even higher carrying capacity (displaying 10,000 or more chimeric molecules on their surface) and lack the highly antigenic (competing) components found on mature phage, i.e., the HOC capsid protein and the tail fibers.

The principle underlying the novel phage display system described herein is illustrated in FIGS. 1A–1D. The basic structure of the schematicized surface lattice is a hexagonal array of hexamers of the major capsid protein gp23*, with a periodicity of 14 nm, to which HOC and SOC bind. The capsid, but not polyheads, has pentamers of another protein, gp24*, at the vertex sites. A HOC monomer binds at the center of each hexamer, and trimers of SOC bind around the trigonal sites, giving equimolarity with gp23*. Unlike the precursor (prohead) state of the surface lattice, which dissociates readily, the mature surface lattice does not dissociate over a wide range of concentrations and environmental conditions (see Black et al., *In Molecular Biology of Bacteriophage T*4, J. Karam Ed., American Society for Microbiology, pp. 218–258, 1994, for the T4 capsid assembly pathway). Moreover, SOC and HOC bind only to the mature state of the surface lattice, and not to the precursor states.

The following examples illustrate the claimed invention, and are not to be considered limiting.

EXAMPLES

The feasibility of the display system described herein, in which molecules of interest are bound to dispensible polypeptides and displayed on a surface lattice protein has been established using C-terminal fusions of three different molecules that vary in size and character. The first, SOC-CYS, has a four-residue extension containing a cysteine residue, which is included to allow the subsequent conjugation of protein ligands (wild-type SOC contains no cysteines). The second, SOC-V3, has a 43-residue sequence containing the V3 loop of human immuno-deficiency virus type-1 (HIV-1), strain IIIB (Laman et al., *J. Virol* 66:1823–1831, 1992), and used CYS to link V3 to SOC. A 12-residue V3 peptide from HIV-1 (strain MN) displayed on filamentous phage has been used successfully to raise neutralizing antibodies (di Marzo Veronese et al., *J. Mol. Biol.* 243:167–172, 1994). The 43 amino acid sequence was chosen because it is comparable in size to individual domains. The third, SOC-VP1, consists of the poliovirus VP1 capsid protein (312 residues), and provides an example of a full length protein.

SOC-VP1 and SOC-V3 were constructed in the same way, as follows.

SOC Fusions: Expression and Phage Genome Integration Vectors

In the first approach, soc-deficient phage were used to infect *E. coli* cells harboring plasmids designed to overexpress SOC-fusion proteins. The progeny phage were expected to bind directly the display proteins. Driven by the T7 promoter (Studier et al., *Methods Enzymol.* 185:60–89, 1990), the soc gene on plasmid pE-SOC (FIG. 2A, panel i) produced high levels of SOC protein. As shown in FIG. 3 (see lanes 6 and 7), more then 10% of the total cellular protein was SOC. However, high level soc expression resulted in inclusion body formation, and the plasmid-containing bacteria rapidly lost the ability to support phage multiplication. Moreover, the SOC that remained soluble was degraded rapidly by proteolytic activity, even in protease-deficient strains of *E. coli*.

Accordingly, two alternative strategies were employed. In the first, the overexpressed SOC or SOC-fusion protein was extracted from inclusion bodies, purified, renatured, and then bound in vitro to polyheads or capsids. In the second, the modified soc gene was reintegrated into the T4 genome to achieve regulated soc gene expression and SOC binding to the viral capsid in vivo in the infected bacteria. To reintegrate the soc gene and its derivatives into the phage genome, a modified positive selection plasmid, pRH, was constructed (FIG. 2B, panel i; see also Hong and Black, Gene 136:193–198, 1993). pRH allows homologous recombination at both ends of soc with the T4–Z1 phage, which is deleted for genes soc, IPIII, IPII, and a part of e". The T4 soc integration vector, pRH, was constructed as follows.

Construction of T4 soc Integration Vector, pRH

In this example of construction, the soc gene is flanked on its 5' side by a 3' portion of the e' (lysozyme) gene of phage T4, and by the strong IPIII promoter to drive soc expression; IPIII is expressed throughout T4 infection, leading to incorporation of about 400 copies of IPIII per head (Black, supra). At the 3' end of soc, a portion of a downstream T4 gene, denV', allows homologous recombination between the phage and plasmid on either side of the soc gene (FIG. 2B, panel i).

The integration vector pRH, which allowed homologous recombination with the T4 derivative Z1, resulted from combining the e'-IPIII-denv' insert, which in turn resulted from digesting plasmid Ep-denv-151 with BamHI and ScaI together with plasmid pA-CYC177. The IPIII gene was removed by digesting at the unique NdeI and EcoRI sites, with soc derivatives inserted at the IPIII position.

Integration vectors pRH-V3 and pRH-VP1 were constructed using pRHB digested with NdeI and EcoRI and filling in the EcoRI end as receptor portion. For the pRH-V3 insert, soc-v3 was digested from pE-V3 with BamHI (which was filled in) and NdeI; for the pRH-VPI insert, pE-VP1 was digested from pE-VP1 with HindIII (then filled in) and NdeI, and ligated to pRH (FIG. 2B, panel i).

The recombination-integration phage T4–Z1 (FIG. 2B, panel ii) is deleted for soc, for a partial 3' overlapping portion (to pRH) of the lysozyme gene e", and for genes IPIII and IPII, which code for dispensable components of the prohead scaffold (Black et al., supra). Absence of both SOC and IPII, which overlap in SDS-PAGE, accounts for the absence from the Z1 phage of a band at the 9 kDa position (FIG. 3, lane 4). Z1 lacks a functional lysozyme gene and requires egg white lysozyme for growth. Homologous recombination can integrate genes from the recombination plasmid at the IPIII position to reconstitute an intact lysozyme (e) gene and allow lysozyme-independent growth. Reintegration of the soc or soc-SII genes at the IPIII position occurred with high frequency in phage-plasmid crosses, as demonstrated by the growth of phage plaques in the absence of egg white lysozyme. Essentially all of these yielded virus particles that contained SOC or SOC-CYS proteins. The SOC-fusion gene recombination bacteriophage, T4–Z1, was constructed as follows.

Construction of soc-fusion Gene Recombination Bacteriophage T4–Z1

T4 phage $(39–56)_{12}$, deleted of ~9.8 kb between genes 39 and d56 (Homyk & Weil, Virology 61:505–523, 1974), (referred to herein as delsoc), was crossed with phage eG326 in E. coli CR63 and tested for egg white lysozyme dependent and independent plating as described by Hong & Black, (Gene 136:193–198, 1993). After two generations of lysozyme-dependent growth, 20 single plaque recombinants were picked at random and the delsoc confirmed by PCR with primers 77 (5'-CTTGGGATCCTAACCAGT-TACTTTCCAC-3'; SEQ ID NO:1; TAG and BamHI tailed) and 95 (5'-CCTGGTGGTCAGGGTYGGAGAAG-GAAGA-3'; SEQ ID NO:2). Similarly, dellPIII was confirmed using primers 67 (5'-AGGAAACATATGAAAA-CATATCAA-3'; SEQ ID NO:3) and 81 (5'-AGAATTACCACGGGCTGCATTAGCAAC-3'; SEQ ID NO:4). The absence of functional gene alt as well as of IPIII and soc from the recombinant phage Z1 (FIG. 2B, panel ii) was determined by SDS-PAGE of purified phage particles (cf. FIG. 3). In addition to the existing soc deletion of 9.8 kb in T4–Z1, the alt gene deficiency allows 6 kb more DNA to be packed into the T4 head (Wu et al., J. Mol. Biol. 218:705–721, 1991).

Expression and Binding to T4 Capsids of a SOC-V3 (HIV-gp 120) Fusion

In the course of the following experiments, certain DNA fragments were amplified by the polymerase chain reaction (PCR), as follows.

DNA Amplification by PCR Techniques

PCR was conducted on several kinds of templates. When T4 plaques were used directly as templates, a single plaque was picked from a plate and suspended in 200 μL of HPLC grade water. A 40-μL aliquot was then boiled for 3 minutes and 25 pmol of each primer was added, together with 15 mmol of each of the four dNTPs, 5 μL of $10\times Mg^{2+}$—containing Taq™ buffer, and 2.5 U AmpliTaq™ DNA polymerase (Perkin Elmer Co). Forty-five thermocycles consisting of incubation at 94° C. for 1 minute; 50° C. for 1 minute, and 72° C. for 4 minutes were performed with a reaction volume of 50 μL, using a modification of the procedure of Eddy and Gold (Genes & Dev. 5:1032–1041, 1991). If a nonpurified phage stock ($>10^{10}$ pfu/mL) was used as template, 1–2 μL was used in place of the single plaque.

The expression vectors used as described below were constructed as follows.

A pET expression vector with phage T7 inducible promoter and T7 translational start signals was modified to allow overproduction of SOC an SOC-fusions in E. coli.

pE-Soc

The soc coding sequence was removed from its normal phage T4 controls (MacDonald et al., Genetics 106:17–27, 1984). The fragment inserted started with the ATG of soc from a PCR product of T4 phage DNA obtained using primers 78 (5'-GAATCATATGGCTAGTACTCGCGGT-3' (NdeI tailed) SEQ ID NO:5) and 77 (SEQ ID NO:1). The PCR product was digested with NdeI and BamHI and then ligated into plasmid pET 3a derivative ppL-1 (Hong & Black, Gene 136:193–198, 1993), which had been digested with NdeI and BamHI to create compatible ends (FIG. 2A, panel i).

pE-S11

The construction of this plasmid was carried out just as described above for pE-SOC, except the inserted fragment was obtained using primers 78 (SEQ ID NO:5) and 84 (5'-AGCAGAATTCAAGCAACCAGTTACTTTC-CACAAATC-3' (tailed with Cys-Leu-Asn-Ser and EcoRI) SEQ ID NO:6), which were trimmed by digestion with NdeI and EcoRI (FIG. 2A, panel ii).

pE-V3

Construction of the pE-V3 plasmid began by digesting pE-Soc with NdeI and BamHI. The V3 insert was obtained by using PCR to amplify the template plasmid pBL21PiNIII, which contains the portion of HIV-1 provirus DNA for gp120, with primers 85 (5'-TGAAGAATTCTGTAGAAAT-TAATTGT-3' (tailed with EcoRI) SEQ-ID NO: 7) and 82 (5'-ATTTGGATCCCTAAATGTTACAATGTGCTTG-3' (tailed with TAG and BamHI) SEQ ID NO:8). The PCR product was digested with EcoRI and BamHI. The soc-Cys insert was excised from pE-S11 with NdeI and EcoRI, and the three DNA pieces were then ligated together (FIG. 2A, panel iii).

pE-VP1

The soc-Cys-Leu-Asn-Ser fragment of pE-S11 was removed with NdeI and EcoRI. A poliovirus vp1 insert was produced by PCR, using template plasmid pSV20, which contained whole poliovirus cDNA and primers 107 (5'-AGCAGAATTCGCTAGCACAGGGGTTA-3' (tailed with EcoRI) SEQ ID NO:9) and 108 (5'-TACAAAGCTTTCTAT-TGGTGTCCGAATCCATATGT-3' tailed with TAG and Hind III) SEQ ID NO:10). The PCR fragment was trimmed by digestion with EcoRI and HindIII, and was ligated to the large fragment derived from pE-SOC by NdeI and HindIII (FIG. 2A, panel iv).

All expression vectors were transformed into *E. coli* HMS174 (DE3), which was induced with 0.5 mM IPTG for 3 hours at 37° C. to test for the desired protein fusions by the procedures described.

The soc-cys peptide extension gene pE-S11 was fused to a portion of the env gene of HIV-1 containing the sequence coding for the V3 loop of gp120. This 43-residue polypeptide contains five amino acids on the N-terminal side of the first cysteine of the loop and two amino acids on the C-terminal side of the second cysteine (Laman et al., *J. Virol.* 66:1823–1831, 1992). This construction allowed high level SOC-V3 expression from the pE-V3 vector (FIG. 2A, panel iii), as determined by SDS-PAGE or Western blotting (FIG. 4B).

The desired recombinant phage could be selected from a cross between the recombination selection phage T4–Z1 and the pRH-V3 plasmid, which contained the SOC-v3 gene, as determined by PCR. The recombination was carried out as follows.

Recombination of Phage T4 Z1 with Integration Vector pRH and its Derivatives

*E. coli* HB101 (pRH-V3) and HB101 (pRH-VP1) were grown in CM medium (Hong & Black, *Gene* 136:193–198, 1993) until the optical density (at 600 nm) reached 0.4. After addition of L-trp to 20 μg/nL, bacteria were infected with T4–Z1 at a multiplicity of infection (MOI) of 4. After 5 hours at 37° C., the infected bacteria were concentrated by centrifugation and suspended in CM medium containing egg white lysozyme and chloroform. The supernatant, after centrifugation for 5 minutes at 4,000×g, was spread on a CM plate containing *E. coli* $B^E$ in CM top agar without lysozyme. Single plaques were isolated and checked for integration of the desired genes using the appropriate PCR primers listed above. The resulting phage were found to contain SOC-V3 (FIG. 4A). Purification was carried out as follows.

Expression and Purification of SOC and SOC-V3

*E. coli* HMS174 (DE3) cells (Studier et al., *Methods Enzymol* 185:60–89, 1990) containing the plasmid pE-V3 were grown in a fermentor at 37° C. When the optical density at 600 nm reached 0.6, the cells were induced with 0.4 mM IPTG for 3–4 hours. The cells were resuspended in 50 mM Tris-HCl (pH 8.0), 50 mM NaCl, 4% glycerol, 3 mM 2-mercapto-ethanol, and 2 mM EDTA (lysis buffer) that contained 100 μg/mL lysozyme. Cells from 6 liters of culture were lysed by three cycles of freezing and thawing. DNase was added (10 μg/mL) to reduce viscosity, and the suspension was centrifuged at 10,000×g for 45 minutes. The pellet fraction, which contained the insoluble SOC protein, was washed twice by suspensions into 100 mM Tris-HCl, followed by centrifugations at 10,000×g for 30 minutes. The washed pellet was extracted with 40 mL of 50 mM Tris-HCl (pH 8.0), containing 6 M guanidine-HCl and 10 mM dithiothreitol. The solution was filtered through a 0.45 μm filter unit and applied to a Superdex 200 preparative grade 60/600 column (6-cm diameter X 60-cm long "6×60 cm"), equilibrated in 20 mM Tris-HCl (pH 8.0), containing 4 M guanidine-HCl and 5 mM DTT (column buffer A). Fractions were assayed by SDS-PAGE (18% acrylamide gels from Novex) after removing the guanidine-HCl (Pepinsky, *Anal. Biochem.* 195:177–181, 1990). Pooled fractions (~90 mL) were concentrated to 35 mL by ultrafiltration using an Amicon stirred cell with a PM10 diaflo™ membrane, and applied to a Superdex™ 75 prep grade 60/600 column (6×60 cm) equilibrated in column buffer A. Fractions were pooled (approximately 90 mL at 0.5 mg/mL), and stored in aliquots at −80° C.

Protein was folded by slowly diluting 25 mL lots into 100 mL of 100 mM sodium phosphate (pH 7.5), containing 5 M urea and 1 mM $MgSO_4$. The diluted protein (~0.12 mg/mL) was dialyzed against two changes of 2 L of buffer minus urea. For folding the SOC-V3 fusion protein, 1–2 mM dithio-threitol was included in the dilution buffer. The clear solution was concentrated to 1–2 mg/mL using an Amicon centriprep-3™ concentrator and then sterile filtered with a Millipore GV 0.22-μm filter unit.

Protein concentrations were determined by UV-spectroscopy (Wetlaufer, *Adv. Protein Chem.* 17:303–390, 1963). The 79-residue SOC protein ($M_T$ 8,989) and the 126-residue SOV-V3 fusion protein ($M_r$ 14,208) both have calculated extinction coefficients of 18 $MM^{-1} \cdot cm^{-1}$. N-terminal sequencing (1–20 cycles) of the wild-type and fusion SOC proteins revealed the sequences one would predict from the translations of the respective coding DNA. The initiating N-terminal methionines in both proteins had been removed by the *E. coli* processing enzymes.

According to SDS-PAGE, the apparent molecular weights of the proteins produced from the expression and recombination vectors and those bound to the phage were the same (i.e., approximately 14,000). These Z1-soc-v3 phage contained about one third of the normal complement of SOC-V3 (i.e., approximately 300 copies per virion), according to quantitation of the Coomassie blue-stained gel (FIG. 4A). Purification of the recombinant phage by CsC1 gradient centrifugation did not significantly reduce the amount of SOC-V3 relative to gp23* (cf. lanes 4 and 5), supporting the inference that SOC-V3 is indeed bound to the phage particles. Comparable amounts of phage were analyzed, as judged by the quantity of the major capsid protein (gp23*) in the Z1, Z1-soc-v3, and wild-type phages (lane 6), which allow comparison of SOC content.

Western blotting with a monoclonal anti-gp120 antibody confirmed the identity of the designated gel band as SOC-V3 (FIG. 4B, lanes 1 and 2). In fact, two closely migrating bands of SOC-V3 were observed, especially with CsC1-purified phage, which may reflect partial proteolysis. Western blotting was carried out as follows.

Gel Electrophoresis and Western Blotting

Phage T4–soc, T4–soc-v3, and T4–soc-vp1 were electrophoresed on 17% (or 13% for T4–soc-vp1) SDS-polyacrylamide gels, transferred to nitrocellulose membranes, and reacted with antibody, using an ECL chemiluminescence kit (Amersham Life Sciences) for detection. Typically, 20–50 μg of each protein were loaded per lane. The antibodies used were: monoclonal Mab902, which is specific for the V3 loop of gp120 from the LAI isolate of HIV-1 (Cheesebro and Wehrly, *J. Virol* 62:3779–3788, 1988); and polyclonal antibody prepared against SDS-PAGE-purified VP1 of poliovirus.

To quantitate the protein on the gels, photographic negatives were digitized using a COHU CCD camera and normalized relative to a Kodak stepwedge. Two-dimensional integration of bands and background subtractions were performed using PIC software (Trus et al., *J. Struc. Biol.* 116:61–67, 1996).

Figure 5B:
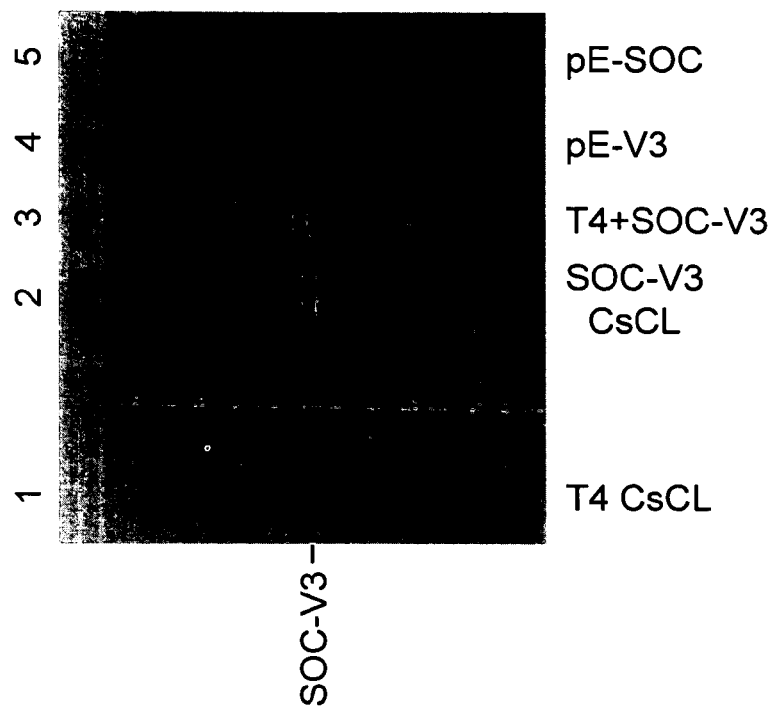
FIGS. 5A and 5B are a pair of photographs of an SDS-polyacrylamide gel, stained to reveal protein (FIG. 5A), and a Western blot (FIG. 5B) of the same samples. SOC-V3 protein was separated by CsC1 gradient centrifugation of T4–SOC$^+$ phage. Protein extracts of bacteria induced for SOC-V3 (PE-V3, lane 4) or SOC (PE-SOC, lane 5) were prepared as described herein; a mixture of SOC-V3 extract and T4–SOC$^+$ phage (T4+SOC-V3, lane 3) was centrifuged at 35,000 rpm for 20 hours. Visible and widely separated bands containing phage ($\rho$~1.5) (T4 CsC1, lane 1) and protein ($\rho$~1.35) (SOC-V3 CsC1, lane 2) were collected, dialyzed, and analyzed by SDS-PAGE. Lane 6 contains molecular weight standards of 3.0, 6.5, 14.3, 21.5, 30, and 46 kDa. The same samples were examined following Western blotting using antiserum against gp120 of HIV-1 (FIG. 5B).
Figure 5A:
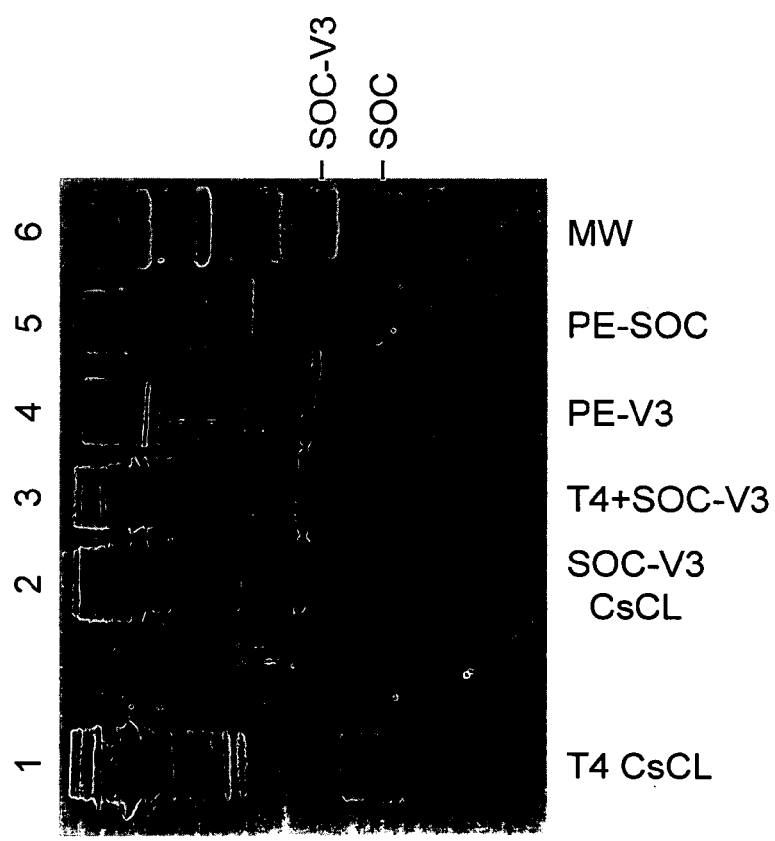

The ability of SOC-V3 to specifically bind to the virion was shown by a mixing experiment (FIG. 5). Purified SOC-containing virions were mixed with SOC-V3 extract (lane 3) and subjected to CsC1 density gradient centrifugation. SOC-V3 was found in the protein band (lane 2), cleanly separated from the much denser phage particles (lane 1). Thus, SOC-V3 did not associate with these virions because their specific SOC binding sites were already occupied, and SOC-V3 does not bind nonspecifically to the capsid surface lattice.

Immunogenicity of SOC-V3 Phase

Female BALB/cj mice that were 6–8 weeks of age were purchased from Jackson Laboratories (Bar Harbor, Me.). A blood sample was obtained from each mouse to provide a negative control sample (denoted "pre-bleeds" in FIG. 6), and the mice were immunized three days later.

Immunizations

Groups of five mice were each immunized with $1\times10^{11}$ PFU of CsC1-purified phage that were emulsified with an equal volume of Freund's Complete Adjuvant containing 1 mg/mL *Mycobacterium tuberculosis* H37Ra (Difco Laboratories, Detroit, Mich.). A total of 100 µL of this emulsion was inoculated subcutaneously on the dorsal hind quarters of each mouse. Secondary immunizations were given intraperitoneally, using the same number of phage particles, in Incomplete Freund's Adjuvant (Difco), and tertiary immunizations were administered in phosphate-buffered saline (140 mM NaCl, 10 mM $PO_4$, pH 7.4). Blood samples were obtained via the tail vein, and the sera were stored at $-20°$ C. until they could be evaluated for anti-gp120 antibodies.

Measurement of Serum Antibody Responses to gp120

Anti-gp120 antibody responses were measured according to a modified (Abacioglu et al., *AIDS Res. Hum. Retrov.* 10:371–382, 1994) form of the antigen-capture ELISA assay (Moore and Jarrett, *AIDS Res. Hum. Retrov.* 5:369–379, 1995). Briefly, native gp120 (Intracel Corp., Cambridge, Mass.) was captured onto polystyrene ELISA trays using an affinity-purified sheep antibody specific for the C terminus of gp120. Mouse sera were titrated in ½-log dilutions, beginning at 0.5 log. Binding was detected using alkaline phosphatase-conjugated goat anti-mouse IgG antibodies (Southern Biotechnology, Birmingham, Ala.) and an enhance™ phosphatase substrate system (Life Sciences Inc., Gaithersburg, Md.).

Figure 6:
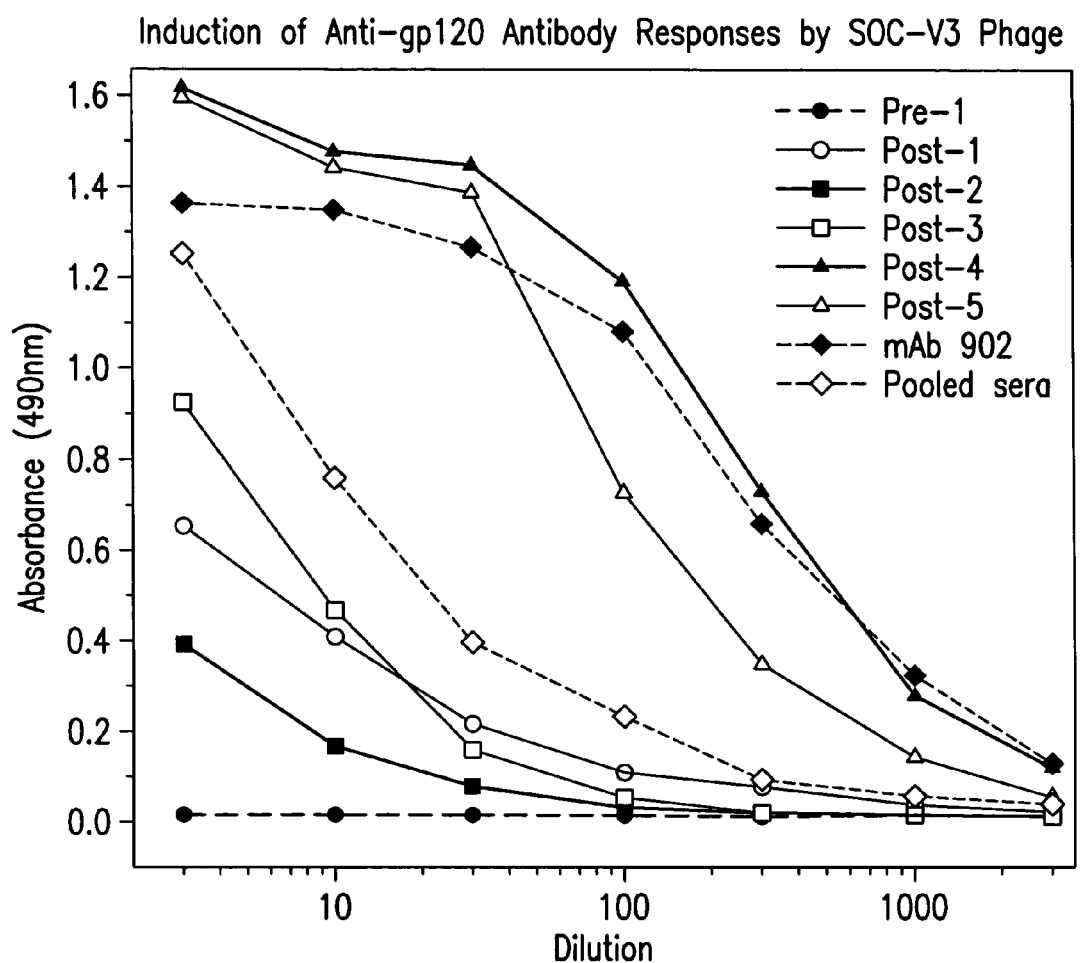
FIG. 6. is a line graph illustrating induction of anti-gp120 antibodies by inoculation of mice with T4 SOC-V3-displaying phage. Individual responses of five animals are shown (○, ■, □, ▲, ∆), as is the baseline of the pre-bleed titer of one mouse (●), which was typical of the whole group. Pooled sera data (open diamond) represent results obtained after pooling the sera collected from all five mice on day 120, following a second boost on day 104.

This assay is configured for selective detection of immune responses to epitopes expressed on the surface of properly folded, glycosylated gp120. The epitope studied is lost when gp120 is denatured (Cheesebro and Wehrly, *J. Virol.* 62:3779–3788, 1988). After purified SOC-V3 phage were used to immunize mice, high levels of anti-gp120 antibodies were observed (FIG. 6). Whereas none of the mice had serum IgG antibodies specific for gp120 prior to immunization, each mouse developed such antibodies after the second inoculation (FIG. 6). The mouse-to-mouse variation seen in these ELISA reactions is typical of serum IgG responses in immunized populations. These data show that immunization with the display phage induced serum IgG antibodies that recognize native glycosylated gp120. Furthermore, these responses were maintained for at least 120 days after the first immunization (FIG. 6). Together, these data demonstrate that protein domains displayed on SOC can be highly immunogenic, inducing antibodies that recognize the native parent protein.

In vitro Binding of SOC-V3 to Polyheads

The bacteriophage T4 capsid is first assembled as a precursor particle called a prohead, which is ~18% smaller in scale than the mature capsid. The prohead contains the full complement of the major capsid protein, appropriately arranged in a prolate icosahedral surface lattice (for review, see Eiserling pp. 11–24 and Black et al., pp. 219–245 In Bacteriophage T4 (Mathews et al., eds.), American Society for Microbiology, Washington, D.C., 1983). This protein, gp23 (521 amino acids of known sequence; Parker et al., *J. Mol. Biol.* 180:399–416, 1984), is present in the mature capsid in a proteolytically modified form, gp23*, with 65 residues (the so-called Δ-region, or gp23-Δ) removed from its amino terminus (Tsugita et al., *J. Mol. Biol.* 98:271–275, 1975; Parker et al., supra 1984). After completion of assembly, the prohead undergoes a radical structural transformation which is responsible not only for the increased size of the mature capsid but also for the other striking differences, which include structural, functional, and immunological differences between mature capsid and the prohead capsoid (for review see Kellenberger *Biosystems* 12:201–223, 1980). This maturation-dependent capsid expansion appears to be a generic feature, common to the assembly pathways of most, if not all, icosahedral dsDNA phages. However, proteolysis of the major capsid protein is not a universal prerequisite for capsid expansion, occurring in some systems (e.g., T-even, P2) but not others (e.g. λ, P22, T3/T7). Functionally, this expansion transformation confers one or more of the following advantages: (1) it stabilizes the relatively labile prohead against breakdown either by dissociating conditions encountered in the environment or by internal pressure exerted by packaged DNA; (2) it greatly increases the internal capacity for DNA, by ~65%; (3) it drives the head-assembly reaction toward the accumulation of more complete particles (Ross et al., *J. Mol. Biol.* 183:353–364, 1985).

To examine the binding of SOC and SOC-V3 to the gp23* capsid surface lattice, polyheads were used. Cleaved/expanded polyheads were prepared and purified as described by Steven et al. (*Biochemistry* 29:5556–5561, 1990; see also Steven et al. *J. Mol. Biol.* 106:187–221, 1976, and Ross et al., *J. Mol. Biol.* 183:353–364, 1985). In brief, polyheads are generally prepared as follows.

Precursor polyheads can be produced by growing the mutant T4.22(amE209) in *Escherichia coli* $B^E$. The purification procedure described by Ross et al. (supra) is supplemented by a final step in which the polyheads were centrifuged through a sucrose/CsC1 step gradient. The polyhead-containing fraction is then dialyzed against SCB buffer (0.1 M $KHPO_4$, 1 mM $MgSO_4$, pH 7.0) at $20°$ C. and then washed twice in the same buffer, pelleted by centrifugation followed by resuspension of the pellet in the same buffer. Mature polyheads are produced by following the procedure of Ross et al. (supra), except that pronase E (Sigma Chemical Co., St. Louis, Mo.) at 0.25 µg/mL can be added to the lysate. Finally, after the expanded polyheads have been isolated and subjected to "SDS cleaning" (Steven et al., supra, 1976), residual amounts of incompletely cleaved gp23 can be converted to gp23* by incubation for 1 hour at $37°$ C. in the presence of 0.1 mg/mL trypsin (Sigma).

Uncleaved, expanded polyheads can be produced as follows. Drops of 2.5 M guanidine hydrochloride (Gdn-HCl) are added to a suspension of purified precursor polyheads (1.5 mg/mL protein in SCB) at room temperature (~20° C.), to a final concentration of 0.25 M Gdn-HCl. Phenylmethanesulfonyl fluoride (PMSF) is added, to 1 mM, and the polyheads are incubated for 30 minutes, then transferred to 4° C. for 3 hours, and dialyzed against 10 mM potassium phosphate (pH 7.0). The polyheads are dialyzed for 2 hours at 4° C., with one change of dialysis buffer. Finally, the sample is centrifuged at 18,000 rpm in a Sorvall SS-34 rotor for 40 minutes at 4° C., and the pellet is overlaid with a small volume of SCB, allowed to resuspend overnight, and finally diluted to the desired concentration in SCB. The resulting preparation is routinely assayed by SDS-PAGE of boiled and unboiled samples, and by negative staining electron microscopy.

For the complementation experiments described herein, 100-μg aliquots of polyheads initially at ~3.5 mg/mL protein in a buffer consisting of 0.1 M potassium phosphate, 1 mM MgSO4, (pH 7.0) were added to a twofold molar excess of SOC or SOC-V3 in a total volume of 100 μL, incubated at 37° C. for 30 minutes, then centrifuged at 20,000 rpm for 30 minutes in the SS34 rotor of a Sorvall RC5B centrifuge. The pellet was resuspended in 0.5 mL of the same buffer, then pelleted again. The resuspended pellet was analyzed by SDS-PAGE with 10–20 μg protein per lane, and the protein was detected by staining with Coomassie brilliant blue.

Negative staining electron microscopy with 1% uranyl acetate was performed on a Philips EM400T electron microscope, with micrographs recorded at a nominal magnification of 46,000×. Optical diffraction and micrograph digitization were conducted as described by Ross et al. (*J. Mol. Biol.* 183:353–364, 1985). Image averaging by computational lattice filtering was performed using the PIC program (Trus et al., *J. Struc Biol.* 116:61–67, 1996), running on an Alpha workstation (Digital Equipment Corp., Maynard, Mass.).

Figure 7:
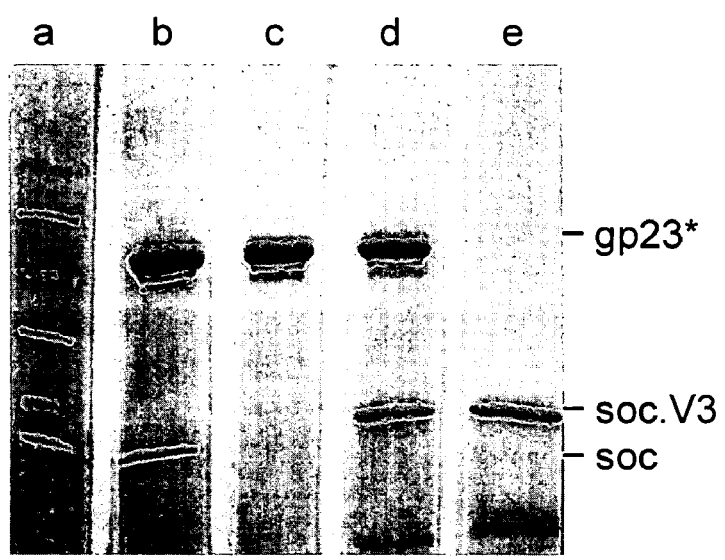
FIG. 7. is a photograph of an SDS-polyacrylamide gel, through which the following samples had been electrophoresed: T4 polyheads complemented with purified SOC (lane b), control (lane c), and SOC-V3 (lane d). Purified SOC-V3 is shown in lane (e), and molecular weight standards (97, 66, 43, 31, 22, and 14 kDa) appear in lane (a).

As with capsids, only polyheads that have undergone the maturational expansion transformation bind SOC (see review by Black et al., supra). As described above, expanded gp23* polyheads were prepared and incubated in the presence of a twofold molar excess of freshly purified SOC-V3 or SOC, then centrifuged to separate them from unbound protein. The resulting pellets were resuspended and examined by SDS-PAGE (FIG. 7). Polyheads are of the cleaved/ expanded type, in which the surface lattice of the major capsid protein gp23 has undergone proteolytic cleavage to the gp23* form and the subsequent expansion transformation, and thus can bind SOC. Quantitation of the SOC and gp23* bands (FIG. 7, lane b) yielded an estimate of 1.2 for the molar ratio of SOC:gp23*. Because the intensity of the gp23* band was close to saturation, FIG. 7 is not significantly discordant with the known equimolarity of SOC and gp23*. The corresponding figure determined for SOC-V3: gp23* (FIG. 7, lane d) was 1.8. However, SOC-V3 is less soluble than SOC and a control incubation of SOC-V3 in the absence of polyheads also produced a pellet (FIG. 7, lane e), unlike the SOC control.

To ascertain whether SOC-V3 was associating specifically with the polyheads, negatively stained electron micrographs were recorded (e.g., FIGS. 8A and 8B), and examined by optical diffraction and image analysis, as described above. The resulting diffraction patterns were found to have a different intensity distribution from those of unlabeled polyheads, implying that SOC-V3 was bound at specific sites and not randomly deposited on the polyhead surface. Filtered images revealed hexamers of stain-excluding units, surrounded by triplets of similarly sized units (FIG. 8C). For comparison, gp23* surface lattices with and without SOC are shown in FIGS. 8E and 8D, respectively. Triplets of SOC binding sites surround the points of local three-fold symmetry in the hexagonal surface lattice (FIG. 8E). In the SOC-V3 binding experiment (FIG. 8C), these sites are occupied by stain-excluding units that are somewhat larger than those observed with wild-type SOC, consistent with the greater size of the SOC-V3 fusion protein. Occupancy of the SOC sites by SOC-V3 molecules is complete or close to it, because the peak density above background of the SOC-V3-related units in FIG. 8C is, on average, 10–15% higher than for the gp23* related units. These results show that the SOC-V3 fusion protein associates specifically with the SOC binding sites. In FIG. 8E, the hexameric units, which represent protruding portions of gp23* molecules, are somewhat larger than the triplet units, which represent SOC monomers. In contrast, the two kinds of stain-excluding units (hexamer and triplet) are similar in size in the SOC-V3-decorated lattice (FIG. 8C), consistent with SOC-V3 being ~50% larger than SOC. Thus, in the incubation experiment (FIG. 8D), the SOC-V3 protein bound rapidly to the available SOC binding sites, and the remainder precipitated.

Construction and Display on Phage T4 of a SOC-VP1 (Poliovirus) Fusion

To test the suitability of this system for display of larger polypeptides, the 312-residue VP1 of the Mahoney strain of poliovirus was displayed (Kitamura et al., *Nature* 291: 547–553, 1981). VP1 is the major capsid immunogen (van der Werf et al., *Proc Natl Acad Sci USA* 80:5080–5084, 1983; Li et al., *J. Virol.* 68:3965–3970, 1994). The SOC-VP1 fusion was constructed by the same procedures as described above, i.e., an expression plasmid producing SOC-VP1 (pE-VP1) and an integration plasmid form of the gene fusion (pRH-VP1) were produced (FIG. 2A, panel iv; FIG. 2B, panel i). A PCR assay confirmed that the soc-vp1 gene fusion had been inserted correctly into both vectors.

The expression vector was found to overproduce SOC-VP1 (FIGS. 9A and 9B). Following integration of plasmid pRH-VP1 into T4–Z1, recombinant SOC-VP1 (43 kDa) was found to be associated with the Z1-soc-vp1 virions, and was retained through purification on CsCl gradients (FIGS. 9A and 9B). As with SOC-V3, a doublet of SOC-VP1 was observed by SDS-PAGE. The amount of display protein bound, cumulatively 25–100 molecules per virion, was considerably lower than with SOC-V3. This could reflect impaired binding, poor expression of the soc-vp1 gene, or instability of SOC-VP1 in *E. coli*. The latter explanation is favored because the integration vector produced predominantly a protein of a size corresponding to the original VP1, and only a smaller amount of the fusion protein (FIG. 9B, lanes 3 and 6), whereas the expression vector produced large amounts of the SOC-VP1 fusion of the expected 43-kDa molecular weight, and low amounts of VP1 (FIG. 9B, lanes 6 and 7). In fact, phage T4 infection protects some foreign proteins from proteolysis in *E. coli* (Hong et al., *Gene* 162: 5–11, 1995), and the recombinant phage clearly displayed significant levels of SOC-VP1, as confirmed below.

Selection of the VP1 Fusion Clone by a Modified Biopanning Procedure

To validate SOC and its gene for immunoselection, it is important to demonstrate that a recombinant phage displaying an epitope of interest can be isolated and propagated (Parmley and Smith, *Gene* 73:305–318, 1988). Results obtained with a modified biopanning procedure employing the Z1-soc-vp1 phage (FIG. 10) show that the displayed VP1 protein is present and immunologically recognizable. The biopanning was carried out as follows.

Biopanning

A mixture of 5×10³ T4–soc-vp1 and 5×10⁹ delsoc in phage dilution buffer (1 mL) was mixed with 30 μL of VP1 antiserum at 4° C. overnight. Thirty μL of 100 mg/mL Protein A-Sepharose CL-4B (Pharmacia) were then added, mixed gently on a rocking platform at room temperature for 30 minutes, and centrifuged at 2,000×g for 2 minutes in an Eppendorf microfuge. The pellet was washed five times by resuspending in 1 mL of SM buffer for 1 minute and centrifuging, as before, at 2,000×g. Finally, the pellet was resuspended in 1 mL of *E. coli* B$^E$ at 2×10⁸ bacteria/mL in M9S with gentle shaking for 20 minutes at 30° C., and then 100 μL was plated.

Subsequent cycles of isolation repeated the same procedure using approximately 5×10⁹ phages obtained from the single plate stock. The same procedure was followed using normal rabbit serum and whole phage T4 antisera as controls. Phage were purified by CsC1 density gradient centrifugation. Other phage techniques were as described previously (Hong and Black, Gene 136:193–198, 1993).

These data are further supported by an immunoprecipitation assay in which approximately 1% of the Z1-soc-vp1 phage remained when the VP1 antiserum was used, whereas the control Z1 phage (before recombination) was not depleted significantly.

Figure 10A:
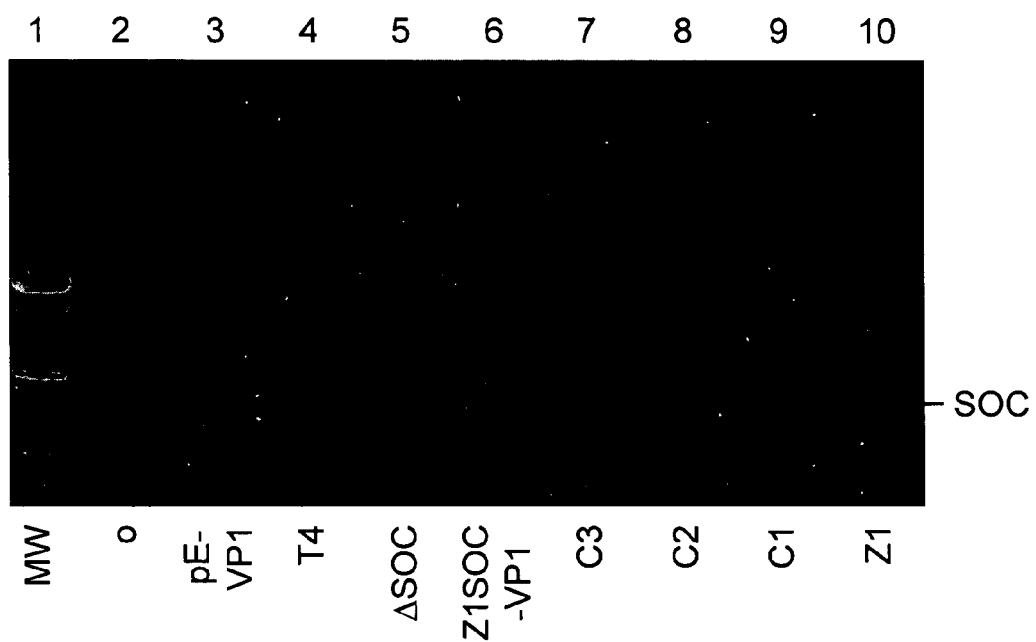
FIGS. 10A and 10B are a pair of photographs of an agarose gel following a PCR assay of a biopanning procedure using an antibody against poliovirus VP1 and an initial mixture of $5 \times 10^9$ delsoc and $5 \times 10^3$ Z1-soc-vpl (FIG. 10A), and a Western blot of the same phage samples stained with anti-VP1 antibody.
Figure 10B:
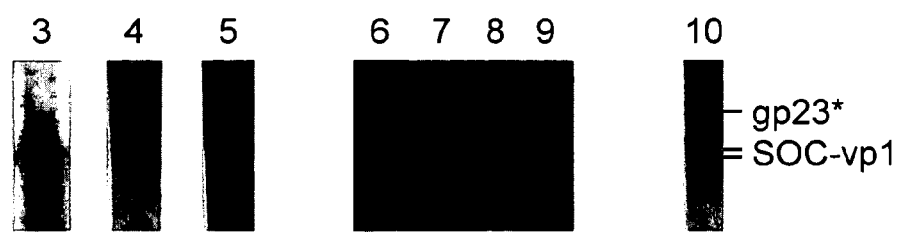

The biopanning procedure began with an initial ratio of one Z1-soc-vp1 phage to 10⁶ delsoc phage. Nevertheless, the desired Z1-soc-vp1 phage could be recognized in the second cycle of selection both by PCR and by Western blotting (FIGS. 10A and 10B). After each of three cycles, the DNA was probed by PCR, using phage DNA as template. A soc band was detected in the second and third cycles (FIG. 10A). In agreement with this measurement, in the second cycle, 1/10 plaques, and in the third cycle, 9/10 plaques contained the soc-vp1 gene, by PCR assay of randomly selected single plaques. Thus, phage of the desired genotype can be selected specifically; presumably, an even smaller fraction than 10–6 could be isolated by using more selection cycles.

As well as being effective, this modified biopanning procedure is both simple and economical (less than 60 μL of antiserum was used).

As demonstrated for SOC-V3 (FIG. 8), this system potentially allows display of proteins on regular arrrays, making them suitable for structural analysis (Unwin, 1993) as well as functional studies.

What is claimed is:

1. A filamentous T4 phage-display system comprising a small outer capsid (SOC) fusion protein or highly antigenic outer capsid (HOC) fusion protein, wherein said fusion protein comprises a molecule of interest fused to the SOC or HOC protein, wherein said SOC or HOC fusion protein is capable of binding to the T4 surface protein gp23 resulting in surface display of the molecule of interest.

2. The composition of claim 1, wherein the molecule of interest is an antigen.

3. The composition of claim 1, wherein the molecule of interest is an enzyme.

4. The composition of claim 1, wherein the molecule of interest is an immunoglobulin.

5. The composition of claim 1, wherein the molecule of interest is a polypeptide.

6. The composition of claim 5, wherein the polypeptide consists of 4 or more amino acids.

7. The composition of claim 1, wherein at least 100 copies of the molecule of interest are displayed on the T4 surface lattice protein array.

* * * * *

SEQUENCE LISTING

```
<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 1
cttgggatcc taaccagtta ctttccac                                            28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 2
cctggtggtc agggtyggag aaggaaga                                            28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 3
aggaaacata tgaaaacata tcaa                                                24

<210> SEQ ID NO 4
<211> LENGTH: 27
<212> TYPE: DNA
<213> ORGANISM: Artificial Sequence
```

```
<220> FEATURE:
<223> OTHER INFORMATION: Description of Artificial Sequence:/ Note =
      synthetic construct

<400> SEQUENCE: 4
agaattacca cgggctgcat tagcaac                                          27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 5
gaatcatatg gctagtactc gcggt                                            25

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 6
agcagaattc aagcaaccag ttactttcca caaatc                                36

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 7
tgaagaattc tgtagaaatt aattgt                                           26

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 8
atttggatcc ctaaatgtta caatgtgctt g                                     31

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:/ Note =
      synthetic construct

<400> SEQUENCE: 9
agcagaattc gctagcacag gggtta                                           26

<210> SEQ ID NO 10
<211> LENGTH: 35
<212> TYPE: DNA
<213> ORGANISM: Artificial Sequence
```

-continued

```
<220> FEATURE:
<223> OTHER INFORMATION: Description of Artificial Sequence:/ Note =
      synthetic construct

<400> SEQUENCE: 10
tacaaagctt tctattggtg tccgaatcca tatgt                              35
```